United States Patent
Hassler, Jr.

(10) Patent No.: US 9,901,383 B2
(45) Date of Patent: *Feb. 27, 2018

(54) CONTROL MODULE FOR A POWERED SURGICAL TOOL, THE MODULE INCLUDING A SHELL HAVING ACTIVE SEALS DISPOSED AROUND THE CONDUCTIVE PINS THAT EXTEND INTO THE SHELL

(71) Applicant: Stryker Corporation, Kalamazoo, MI (US)

(72) Inventor: William L. Hassler, Jr., Portage, MI (US)

(73) Assignee: STRYKER CORPORATION, Kalamazoo, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/057,649

(22) Filed: Mar. 1, 2016

(65) Prior Publication Data

US 2016/0175021 A1    Jun. 23, 2016

Related U.S. Application Data

(60) Division of application No. 13/922,877, filed on Jun. 20, 2013, now Pat. No. 9,295,476, which is a
(Continued)

(51) Int. Cl.
*H01R 13/52* (2006.01)
*A61B 18/00* (2006.01)
(Continued)

(52) U.S. Cl.
CPC .......... *A61B 18/00* (2013.01); *A61B 17/1626* (2013.01); *A61B 18/18* (2013.01);
(Continued)

(58) Field of Classification Search
CPC ............ H01R 13/5219; H01R 13/5202; H01R 13/521; H01R 13/5221; H01R 13/523
(Continued)

(56) References Cited

U.S. PATENT DOCUMENTS 4,041,241 A    8/1977   Olmstead et al.
4,112,953 A *  9/1978   Shanker ............... A61N 1/3752
                                                   439/843
(Continued)

FOREIGN PATENT DOCUMENTS

CN    2369637 Y    3/2000
CN    2538285 Y    3/2003
(Continued)

OTHER PUBLICATIONS

"ISA Search Report & Written Opinion of PCT/US2011/066226 Dated Jul. 30, 2012".

(Continued)

*Primary Examiner* — Abdullah Riyami
*Assistant Examiner* — Vladimir Imas
(74) *Attorney, Agent, or Firm* — Howard & Howard Attorneys PLLC

(57) ABSTRACT

A control module for a powered surgical tool. The module includes a shell. Internal to the shell is a circuit for controlling the power generating unit of the tool with which the module is associated. Conductive pins extend through the shell to provide electrical connections to the components within the shell. Active seals are disposed around the conductors and the inner walls of the shell that define the openings in which the pins are seated. Each active seal include an inner and outer skirt. A biasing component disposed between the skirts urges the inner skirt against the section of the conductive pin seated in the opening. The biasing component also urges the outer skirt against the (Continued)

adjacent opening-defining inner wall of the shell. The active seal functions as a barrier between the conductive pin and the adjacent inner wall of the shell.

24 Claims, 25 Drawing Sheets

Related U.S. Application Data continuation of application No. PCT/US2011/066226, filed on Dec. 20, 2011.

(60) Provisional application No. 61/425,523, filed on Dec. 21, 2010.

(51) Int. Cl.

| | | |
|---|---|---|
| *A61B 17/16* | (2006.01) | |
| *A61B 18/18* | (2006.01) | |
| *H03K 17/97* | (2006.01) | |
| *H05K 5/06* | (2006.01) | |
| *A61B 17/00* | (2006.01) | |

(52) U.S. Cl.
CPC ............. *H03K 17/97* (2013.01); *H05K 5/069* (2013.01); *A61B 2017/00398* (2013.01); *A61B 2017/00725* (2013.01); *A61B 2018/00178* (2013.01); *A61B 2018/00702* (2013.01); *A61B 2018/00916* (2013.01); *A61B 2018/00994* (2013.01)

(58) Field of Classification Search
USPC .......................... 439/271, 909, 462; 318/139
See application file for complete search history.

(56) References Cited

U.S. PATENT DOCUMENTS

| | | | | | |
|---|---|---|---|---|---|
| 4,355,855 | A | * | 10/1982 | Rebikoff | H01R 13/523 439/275 |
| 4,516,820 | A | * | 5/1985 | Kuzma | A61N 1/3754 439/271 |
| 5,265,890 | A | | 11/1993 | Balsells | |
| 5,275,607 | A | * | 1/1994 | Lo | A61B 17/32002 604/22 |
| 5,613,954 | A | * | 3/1997 | Nelson | A61B 17/3421 604/167.03 |
| 5,669,790 | A | * | 9/1997 | Carson | A61N 1/056 439/271 |
| 5,747,953 | A | | 5/1998 | Philipp | |
| 5,755,743 | A | * | 5/1998 | Volz | A61N 1/3754 607/36 |
| 5,782,821 | A | * | 7/1998 | Couch | A61B 46/10 383/71 |
| 5,944,736 | A | * | 8/1999 | Taylor | A61B 17/0206 600/201 |
| 6,006,135 | A | * | 12/1999 | Kast | A61N 1/3752 439/652 |
| 6,029,089 | A | * | 2/2000 | Hawkins | A61N 1/3752 439/271 |
| 6,428,368 | B1 | * | 8/2002 | Hawkins | A61N 1/3752 439/271 |
| 6,984,145 | B1 | * | 1/2006 | Lim | A61N 1/3752 439/462 |
| 7,507,114 | B2 | * | 3/2009 | Kent | H01R 13/508 439/174 |
| 7,611,378 | B1 | * | 11/2009 | Brekosky | H01R 13/5202 439/500 |
| 7,638,958 | B2 | | 12/2009 | Philipp et al. | |
| 7,942,686 | B2 | * | 5/2011 | Boyd | A61N 1/375 439/271 |
| 8,221,433 | B2 | * | 7/2012 | Lozier | A61B 17/068 606/104 |
| 8,758,342 | B2 | * | 6/2014 | Bales | A61B 18/1206 606/48 |
| 9,050,098 | B2 | * | 6/2015 | Deville | A61B 18/1445 |
| 2004/0092991 | A1 | * | 5/2004 | Deng | A61B 17/32002 606/170 |
| 2007/0085496 | A1 | | 4/2007 | Philipp et al. | |
| 2007/0090788 | A1 | | 4/2007 | Hansford et al. | |
| 2008/0020634 | A1 | | 1/2008 | Taniguchi et al. | |
| 2008/0195101 | A1 | * | 8/2008 | Lechot | A61B 17/1617 606/79 |
| 2010/0102517 | A1 | | 4/2010 | Kumar et al. | |
| 2013/0023973 | A1 | * | 1/2013 | Richard | A61N 1/375 607/116 |
| 2014/0187870 | A1 | * | 7/2014 | Weber | A61B 10/0266 600/301 |

FOREIGN PATENT DOCUMENTS

| | | |
|---|---|---|
| DE | 42 21 625 C1 | 4/1993 |
| DE | 196 53 580 A1 | 6/1998 |
| DE | 10 2006 006386 A1 | 8/2007 |
| JP | 3082811 U | 10/2001 |

OTHER PUBLICATIONS

"JP Patent Office, Office Action for JP Pat. App. 2013-546332, Nov. 2015."

* cited by examiner

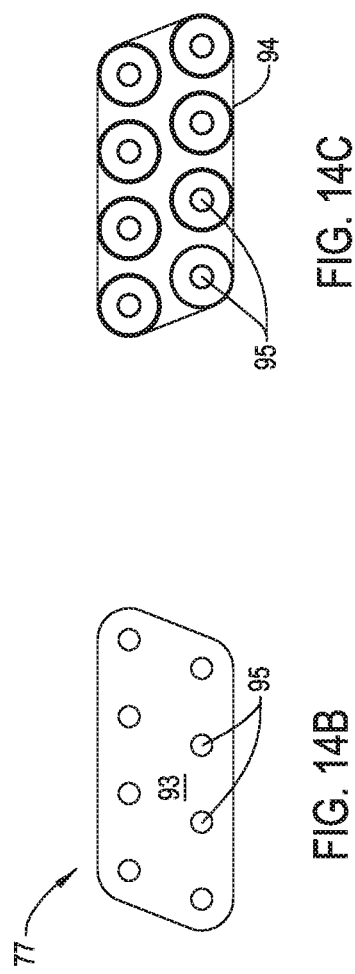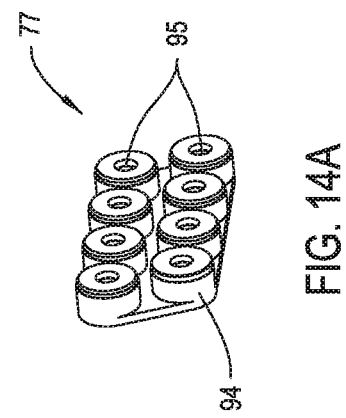

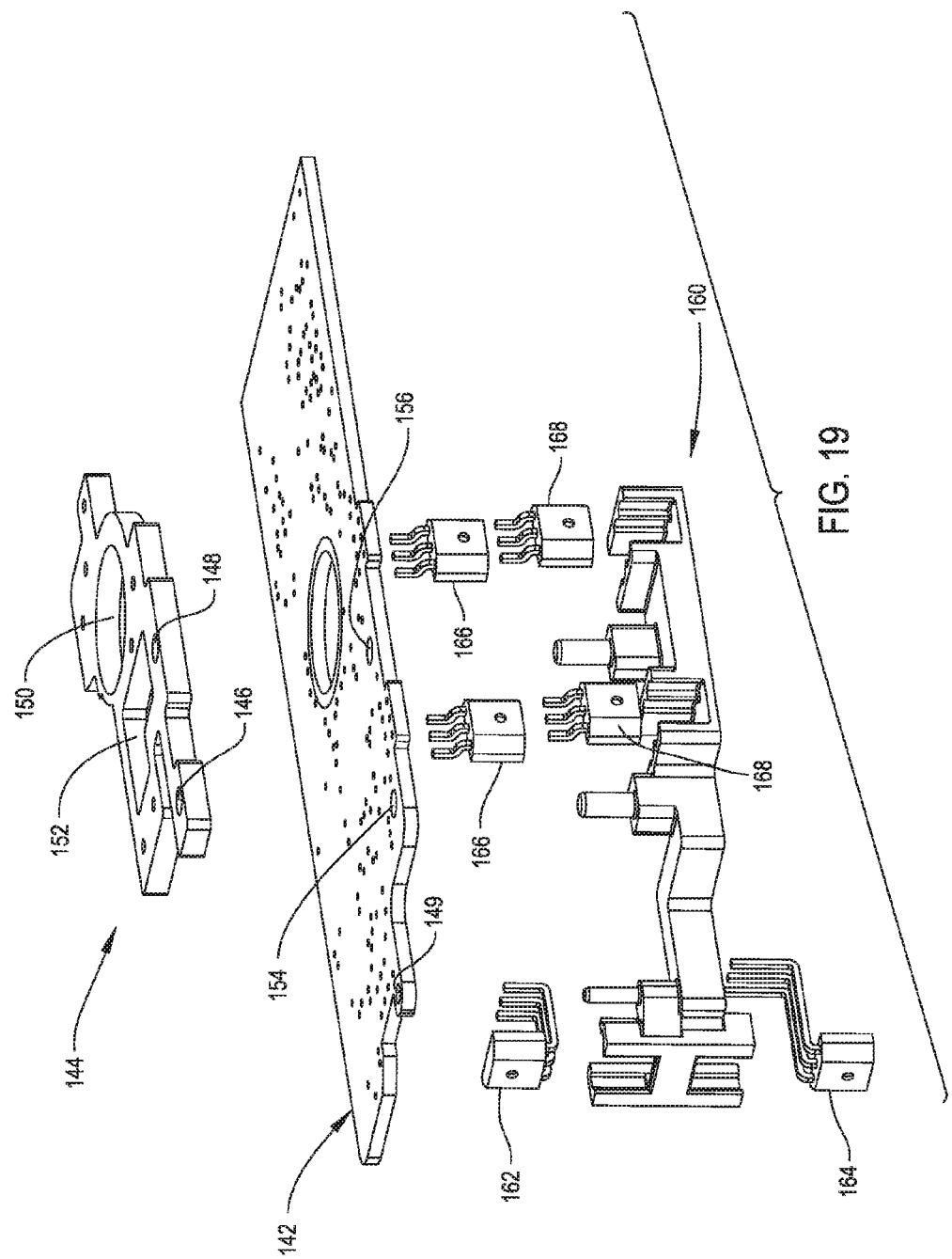

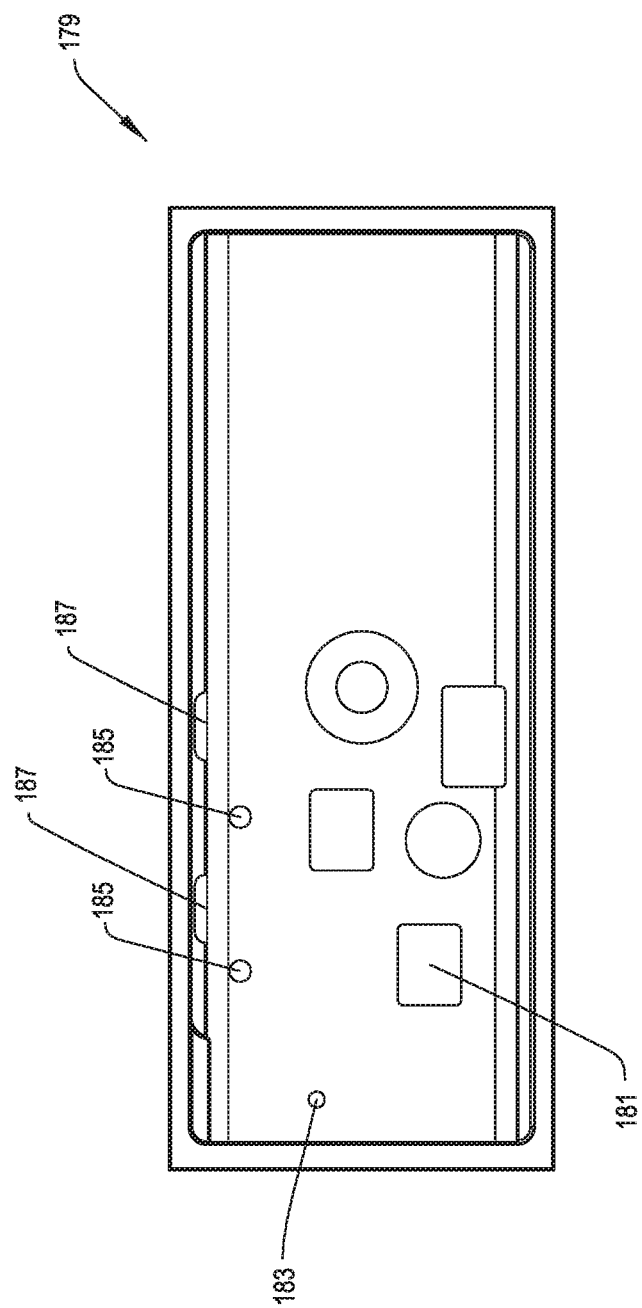

CONTROL MODULE FOR A POWERED SURGICAL TOOL, THE MODULE INCLUDING A SHELL HAVING ACTIVE SEALS DISPOSED AROUND THE CONDUCTIVE PINS THAT EXTEND INTO THE SHELL

RELATIONSHIPS TO EARLIER FILED APPLICATIONS

This application is a divisional of U.S. patent application Ser. No. 13/922,877 filed 20 Jun. 2013, now U.S. Pat. No 9,295,476. application Ser. No. 13/922,877 is a continuation of PCT App. No. PCT/US2011/066226 filed 20 Dec. 2011. PCT App. No. PCT/US2011/06226 claims priority from U.S. Prov. Pat. App. No. 61/425,523 filed 21 Dec. 2010. The contents of the above-identified applications are incorporated herein by reference.

FIELD OF THE INVENTION

This invention is generally related to electrically powered surgical tools. More particularly, this invention relates to a powered surgical tool with a sealed control module in which the circuit that controls the activation of the tool is enclosed.

BACKGROUND OF THE INVENTION

In modern surgery, one of the most important instruments available to medical personnel is the powered surgical tool. Often this tool is in the form of a handpiece in which a motor is housed. Secured to the handpiece are cutting accessories designed for application to a surgical site to perform a specific medical procedure. For example, some powered surgical tools are designed for use with cutting accessories such as drills, burs or reamers for cutting bores into tissue or for selectively removing tissue such as bone. Other powered surgical tools are provided with saw heads. These tools are designed to be used with saw blades or blade cartridges used to separate large sections of hard and soft tissue. A wire driver is a power tool that, as its name implies, drives a wire into a patient, more particularly, a bone. Power tools are also used to perform other functions in the operating room. For example, it is known to use a power tool to mix the components that form a mass of surgical cement.

The ability to use powered surgical tools on a patient lessens the physical strain of surgeons when performing medical procedures on a patient. Moreover, most surgical procedures can be performed more quickly and more accurately with powered surgical tools than with the manual equivalents that preceded them.

One type of powered surgical tool that is especially popular with some physicians is the cordless, battery-operated powered surgical tool. As the name implies, this tool has a battery that serves as the power source for the motor. This eliminates the need to provide the tool with a power cord connected to an external-power source. Elimination of the power cord offers benefits over corded, powered surgical tools. Surgical personnel using this type of tool do not have to concern themselves with either sterilizing a cord so the cord can be introduced into the sterile surgical field or ensuring that, during a procedure, an unsterilized section cord is not inadvertently introduced into the surgical field. Elimination of the cord also results in the like elimination of the physical clutter and field-of-view blockage a cord brings to a surgical procedure.

One feature shared by both corded and cordless power surgical tools is the presence of a control switch or member on the tool. This member is often in the form of a biased switch, trigger or button. A number of corded and cordless surgical tools have handles similar to pistol handgrips. A tool of this shape is sometimes designed so that the control member is a trigger that is slidably mounted with respect to the handle.

Surgical power tools, unlike many other conventional power tools, have to do more than deliver relatively large amounts of power. Surgical power tools must also be compliant with government regulatory agencies and hospital operating room standards for medical surgery. Surgical power tools must be able to withstand repeated exposure to an environment that is saturated with steam and an environment that is very hot. This is because, prior to use, a powered surgical tool is autoclave sterilized. In this process, the tool is placed in a chamber where the atmosphere is saturated steam, the temperature is approximately 135° C. (or 275° F.) and the atmospheric pressure is approximately 207,000 Pa (or 30 psi). Internal components of the tool, including the conductive, electrical components of its control circuit, if left unprotected in and repeatedly exposed to this environment, can corrode or short circuit. A common solution is to have a sealed control module to enclose these internal electrical components in a welded or brazed housing. A problem exists because during the sterilization process these housings are repetitively exposed to both pressurized steam and a vacuum environment. This cyclic pressurizing and depressurizing of the control module causes the walls or panels of the module to repetitively bulge in and out. This repetitive flexure of the module walls/panels results in a fatigued failure of the weld/braze. As a consequence of this failure, steam can enter the module.

The Applicant's Assignee's U.S. Pat. No. 7,638,958, POWERED SURGICAL TOOL WITH CONTROL MODULE THAT CONTAINS A SENSOR FOR REMOTELY MONITORING THE TOOL POWER GENERATING UNIT, issued Dec. 29, 2009, and incorporated herein by reference, discloses one means for protecting the internal components of a surgical power tool from the affects of autoclave sterilization. The tool of this invention has a sealed module that houses the control circuit that regulates tool actuation. The control circuit regulates the actuation of the power generating unit of the surgical tool. The power generating unit emits a signal representative of its operating state. Inside the sealed control module shell is a sensor that monitors the signal emitted by the power generating unit. The control circuit, based on the sensor signal, regulates actuation of the power generating unit. Where the power generating unit is a motor, the signal emitted by the unit is the magnetic field that varies with rotor position. The sensor monitors the strength of this field.

U.S. Pat. No. 5,747,953 also discloses a means for protecting the internal components of a surgical tool from the affects of autoclave sterilization. The tool of this invention has a sealed module that houses the circuit that regulates tool actuation. Also internal to this module, are contactless sensors that monitor the states of externally mounted triggers. Attached to each trigger and located inside the tool housing is a magnet. Internal to the module are magnetic field sensors. Each sensor generates a varying signal as a function of the proximity of an associated one of the trigger magnets. The manual displacement of the trigger results in a like displacement, inside the tool, of the magnet. When a trigger and magnet are so displaced, the complementary sensor generates a signal that indicates the movement has occurred. Upon receipt of this signal, the control circuit generates the signal needed to allow an energization current to be applied to the motor.

The electrically conductive components of the on/off control assembly of the above tool are shielded from the supersaturated steam of the autoclave environment. When this tool is sterilized, these components are not adversely affected.

The control modules of the Applicant's Assignee's U.S. Pat. Nos. 5,747,953 and 7,638,958, both of which are incorporated herein by reference, have proven to be useful for shielding the tool control components and sensors from the effects of autoclave sterilization. However, the modules of both these patents include a housing that is essentially a shell to which a lid is brazed. During the sterilization process, the high pressure vapor imposes a significant pressure on the module housing. This force is known to press, or flex, the panels of the module shell and lid inwardly. Once the pressurized gas is removed from the chamber in which the tool is being sterilized, the gas within the module, which was compressed by the inward flexing of the panels forming the housing, flexes the panels outwardly to their initial state. This repeated in and out flexing of the housing lid weakens the braze that holds the lid to the complementary shell. This weakening of the braze joint can result in its separation. Once the braze separates, steam is able to flow into the module housing. This steam, when it condenses as water, collects on the components internal to the module. This water can corrode or short circuit the components internal to the module so as to render the module itself useless.

Moreover, even the panels of the module of Applicant's Assignee's U.S. Pat. No. 7,638,958 are formed with openings. Plural sets of contact pins extend into this module. A first set of pins function as the conductive paths over which power signals are applied to the module. A second set of conductive pins function as the conductive paths over which the control components internal to the module selectively apply energization signals to the power generating unit integral with the tool. A third set of pins are used to exchange data and control signals with components external to the module. These pins extend through openings in the module housing.

Presently, powered surgical tools utilize ceramic frits to seal the openings of the module housing through which these pins extend. Each frit extends between a pin and the internal wall of the module housing that defines the opening through which the pin extends. Often these frits are tube-shaped. These ceramic frits can withstand the rigors of autoclave sterilization. While these frits provide good seals, they are expensive to manufacture.

SUMMARY OF THE INVENTION

This invention is related to a new and useful powered surgical tool with a control module designed to withstand the rigors of autoclave sterilization. The surgical tool of this invention is designed to provide an internal circuit board, which is sealed so as to avoid malfunction caused by sterilization.

The powered surgical tool of this invention includes a handpiece that contains the power-producing component. Often this component is a DC motor. Also, internal to the handpiece is a module that contains the control circuit that regulates the application of power to the motor. This control circuit is contained in a sealed module.

The components internal to the sealed control module are shielded from the outside environment using active seals. Active seals act as sealing agents around the pins that enter the holes found on the control module housing. An active seal comprises a boot and a spring that collectively form a substantially gas-tight seal between the interior of the control module housing and the external environment. Pins enter through a series of holes found on a single panel of the module housing and into the inside of the control module housing. Active seals are relatively inexpensive to provide.

The control module of this invention further includes a shell to which a lid is attached. A threaded fastener holds the lid to the shell. One or more O-rings are disposed between the lid and the shell. The O-rings form a substantially gas-tight seal between the lid and the shell. The O-rings are able to withstand the rigors of autoclave sterilization.

In one embodiment, the powered surgical tool of this invention is a cordless tool. In other embodiments of this invention, the tool is corded.

Another feature of the tool of this invention is that active seals are disposed around the conductive pins that extend through the module housing. Each active seal functions as a barrier between the pin with which the seal is associated and the inner wall of the housing that defines the opening through which the pin extends.

BRIEF DESCRIPTION OF THE DRAWINGS

The invention is pointed out with particularity in the claims. The above and further features of this invention may be better understood by reference to the following description taken in conjunction with the accompanying drawings in which:

FIG. 14A is a perspective view of the inner retaining cap;

FIG. 14B is a plan view of the inwardly directed face of the inner retaining cap;

FIG. 14C is a plan view of the outwardly directed face of the inner retaining cap;

FIG. 19 is an exploded view of an alternative embodiment of the control module illustrating some of the components mounted to and in the module, including: a mount, a plurality of Hall sensors, a circuit board and a spacer;

FIG. 24 is a plan view of an alternative embodiment of the control module lid illustrating a plurality of recesses.

DETAILED DESCRIPTION

I. First Embodiment

Figure 1:
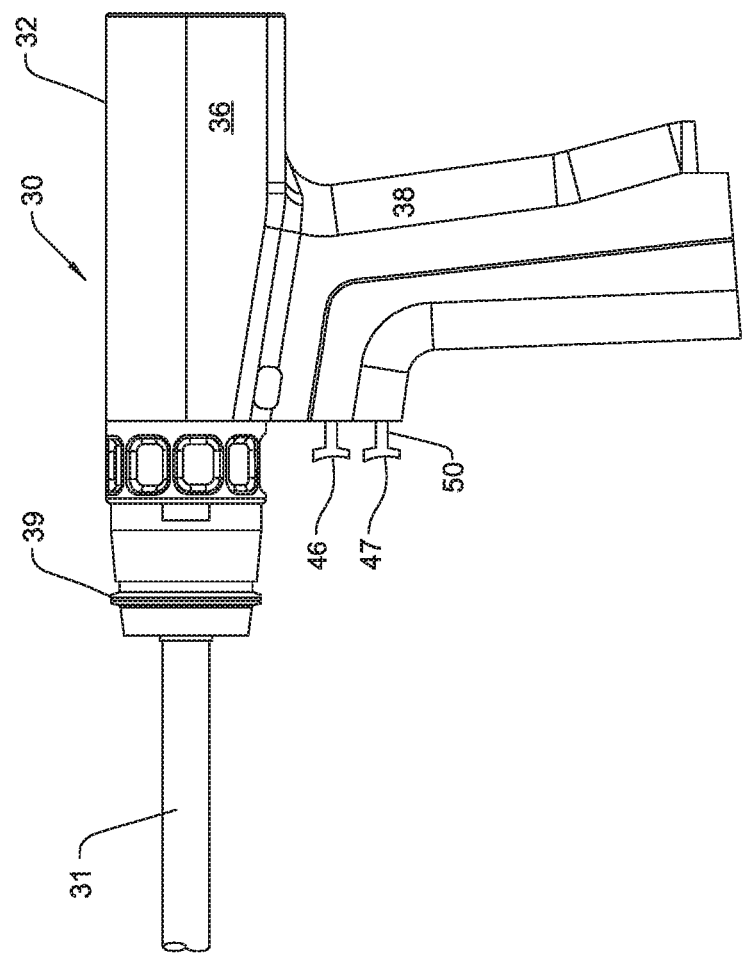
FIG. 1 is a side view of a powered tool incorporating the features of this invention.
Figure 2:
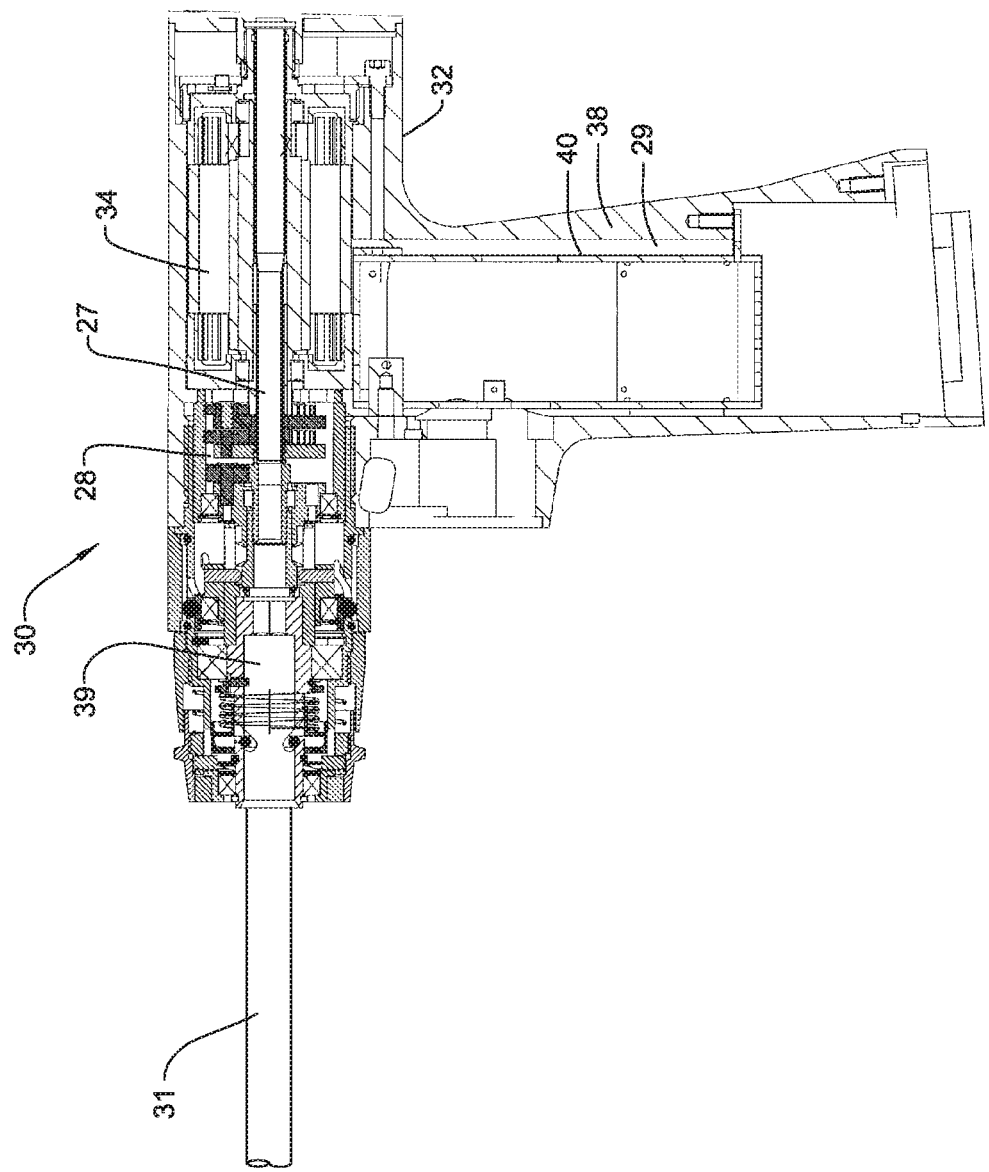
FIG. 2 is a cross sectional view of a powered tool of this invention.

FIGS. 1 and 2 illustrate a power tool 30, a surgical tool, constructed in accordance with this invention. Tool 30 has a housing 32 in which an electrically-actuated power-generating unit is located. In the specific tool 30, this power-generating unit is a brushless, Halless, DC motor 34. Tool housing 32 is shaped to have a generally cylindrical head 36 in which motor 34 is fitted. Extending downwardly from head 36, tool housing 32 is shaped to have a handle 38. Handle 38 is formed to have an internal void space 29. An attachment 31 extends from the housing 32 that is connected to and actuated by the power generating unit 34 for performing a surgical/medical task.

Also contained in the head 36 is a coupling assembly 39 represented by a ring moveably mounted to the front part of housing 32. Coupling assembly 39 consists of the mechanical linkage that releasably attaches a surgical attachment 31 to the motor 34 so that the motor can actuate the attachment 31. In some tool systems of this invention, the attachment is referred to as a cutting accessory. The exact structure of the coupling assembly 39 is not relevant to the structure of this invention. If, as in the tool of FIGS. 1 and 2, the power generating unit is motor 34, coupling assembly 39 consists of a locking arrangement that releasably holds the accessory to the motor shaft 27 so that accessory rotates or oscillates with the rotation of the motor shaft. In some versions of the invention, a speed reduction gear assembly 28 is located between motor 34 and coupling assembly 39.

Disposed inside the handle void space 29 is a sealed control module 40. Control module 40, as discussed below, contains the components that regulate the application of energization current to the motor 34. One circuit that can be employed with this version of the invention is described in the Applicant's Assignee's previously incorporated by reference U.S. Pat. Nos. 5,747,953 and 7,638,958.

Power for energizing the motor 34 is from a battery (not identified). In practice, the battery is removably attached to the butt end of the handle 38. One battery that can be employed with this version of the invention is described in the Applicant's Assignee's U.S. Patent App. Pub. No. 2007/0090788 published on Apr. 26, 2007, and herein incorporated by reference.

Also shown in FIG. 1 are two trigger switches 46 and 47 arranged in tandem extend forward from the front face of the handle 38. Each trigger switch 46 and 47 is slidably mounted to the tool housing 32. Each trigger switch 46 and 47 includes a generally cylindrical barrel 50. The barrel 50 is the portion of the trigger switch 46 or 47 that extends forward of the housing handle 38. Each trigger switch 46 and 47 has a head (not identified), shaped as a fingerhold, and is disposed over the distal free end of the barrel 50. ("Distal", it shall be understood means toward the surgical site to which the tool 30 is directed. "Proximal", means away from the surgical site.) Trigger switches 46 and 47 are mounted to tool housing 32 so that the barrels 50 are located in front and are aligned with the control module 40.

Figure 3:
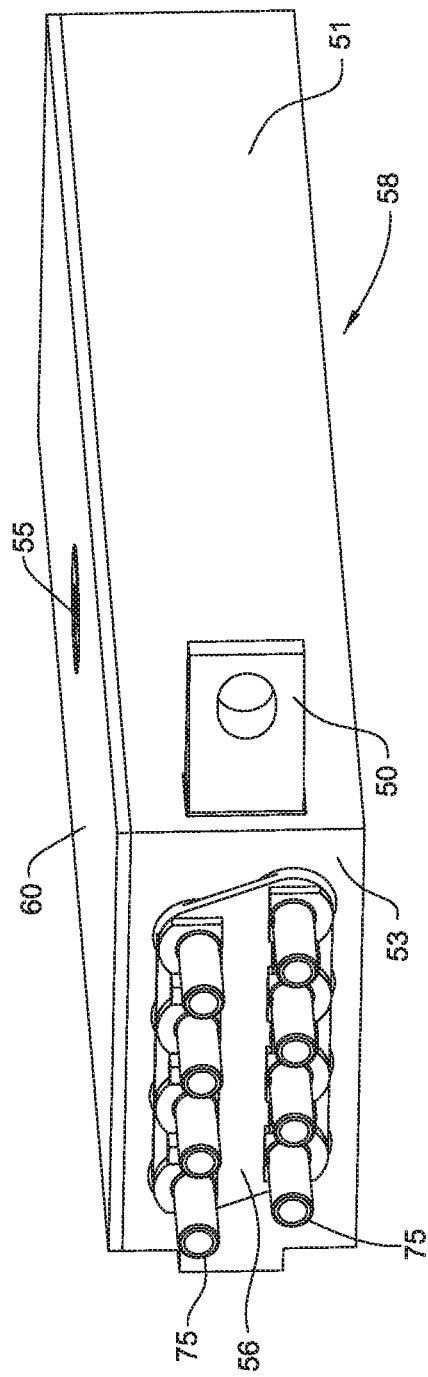
FIG. 3 is a perspective view of the sealed control module with seal assembly.
Figure 4:
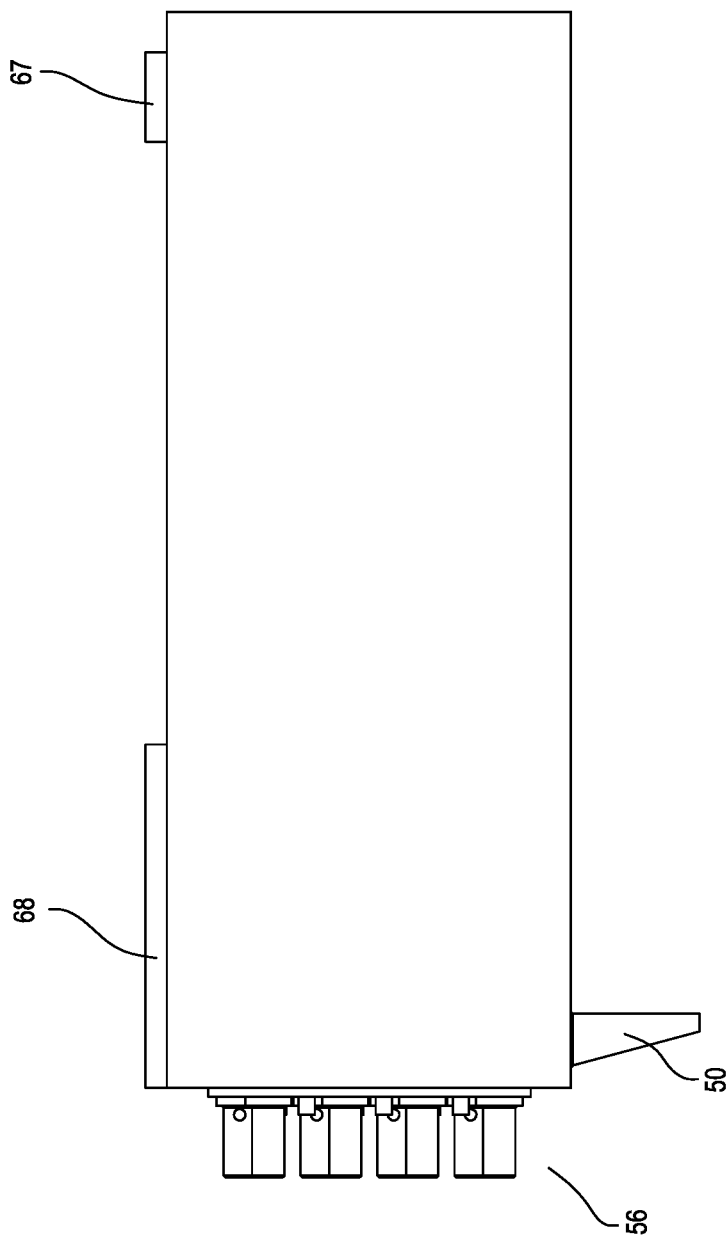
FIG. 4 is a plan view of the top of the control module with seal assembly.

As shown in FIGS. 2, 3 and 4, a tab 50 is used to orient the control module 40 within handle 38 of the tool 30. Tab 50 extends perpendicularly outwardly from side panel 51 of control module 40. The tab 50 is adjacent lower panel 53. The tab 50 is formed with an opening, not identified. Tab 50 serves as a bracket for receiving a fastener (not illustrated) used to hold the control module 40 in the handle 38.

Also shown in FIG. 3, are pins 75 that extend through the shell lower panel 53. The pins 75 provide electrical connections to the components internal to module shell 58. A seal assembly 56 is located on the lower panel 53 for securing pins 75 to control module shell 58. Additionally, lid 60 sits on top of control module shell 58 and is secured to the shell 58 using a threaded fastener 55. Pins 75 extend perpendicularly outward from the lower panel 53 of module shell 58. Pins are secured within seal assembly 56 by a press fit, while the seal assembly is compression fit into the module shell 58. In a preferred embodiment of the invention, the pins 75 are comprised of electrically conductive alloys, such as nickel & gold plated brass.

FIG. 4 is a plan view of the control module 40. FIG. 2 illustrates how the module 40 seats in a void space 29 of handle 38. Pins 75 extend perpendicularly away from the lower part of the control module 40.

Figure 5:
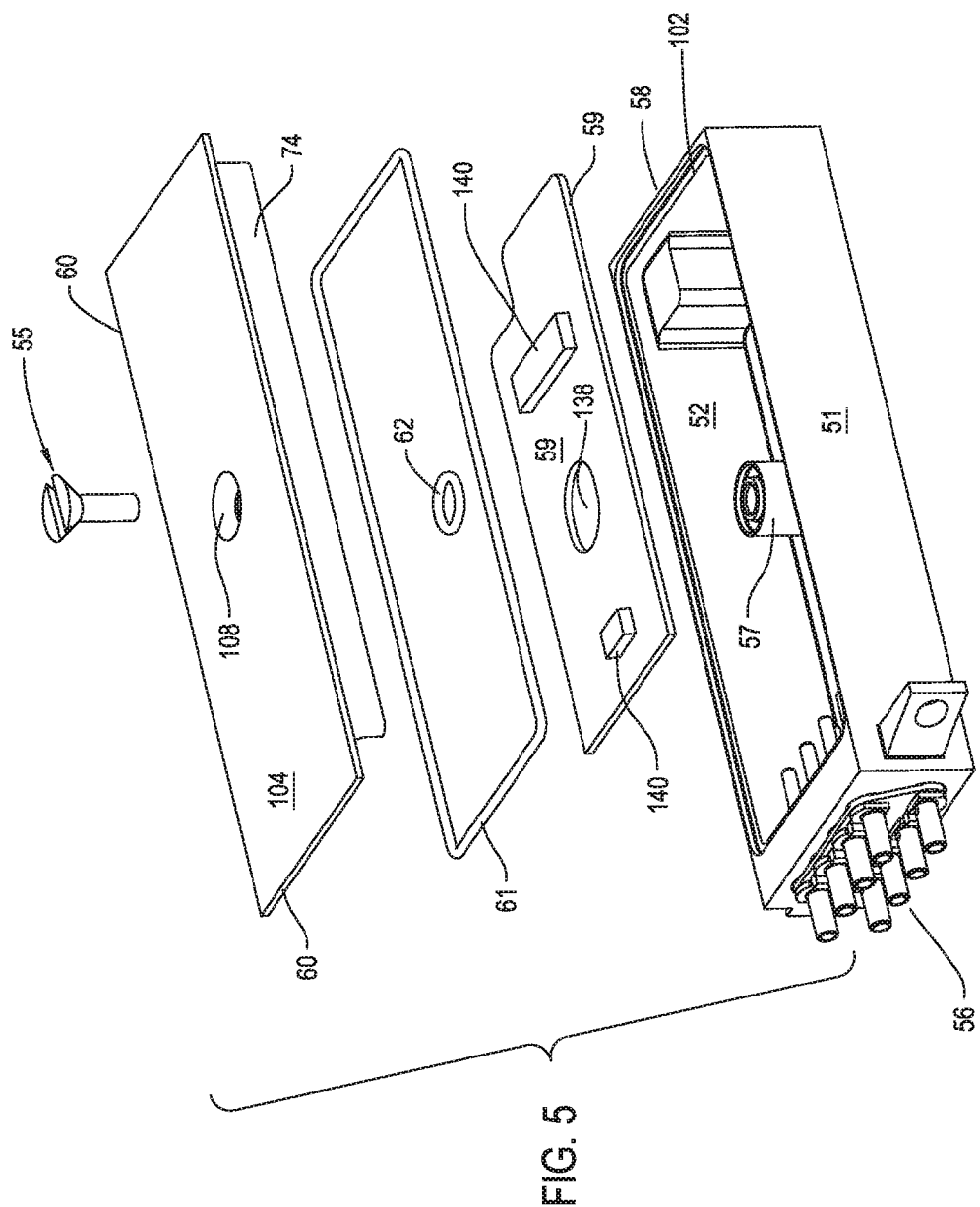
FIG. 5 is an exploded view of the control module illustrating some of the components mounted to and in the module.

The control module 40, now described by initial reference to FIGS. 3-5, includes a housing that consists of a shell 58 and a lid 60. Both the shell 58 and lid 60 are formed from aluminum. In a preferred embodiment of this invention, the shell and the lid 60 are formed from aluminum alloy 7075 T6. This alloy has a yield strength of at least 420 MPa. The control module shell 58 houses a printed circuit board 59. The lid 60 is fastened to the top of the module 50 using a threaded fastener 55. Two O-rings 61 and 62 are disposed between shell 58 and lid 60. Pins 75 extend through openings 69 (FIG. 6A) in the shell 58. The pins 75 provide conductive paths to/from the control components internal to the module 40. A seal assembly 56 forms a set of individual seals around the pins 75.

Figure 17:
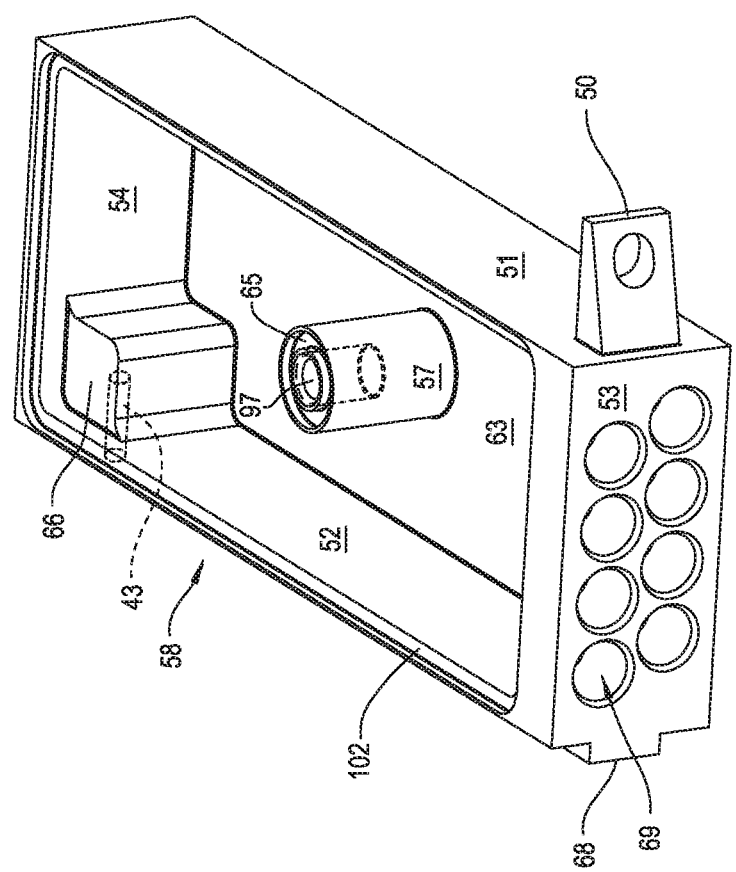
FIG. 17 is a perspective view of the control module shell illustrating the two rows of staggered holes on the lower panel of the shell to accept an active seal assembly.

Control module shell 58, seen best in FIGS. 5 and 17, has five panels, a lower panel 53, a pair of side panels 51 and 52, a top panel 54, and a base panel 63. Base panel 63 is the largest of the panels, panels 51-54 extend perpendicularly outwardly from the edges of the base panel 63. When the control module 40 is seated in the module shell 58, side panel 52 is the most distal of the panels and extends longitudinally inside the handle 38. Lower and top panels 53 and 54, respectively, extend perpendicularly rearward through the handle 38 from the opposed top and bottom edges of the side panel 52. Side panel 51 is the most proximal of the panels. The side panel 51 extends between the proximal ends of the lower and top panels 53 and 54, respectively. The side panel 52 extends between the distal ends of the lower and top panels 53 and 54, respectively.

In the illustrated version of the invention, panels 51 and 52 have a common thickness, the distance between the inner and outer faces, of approximately 1.4 mm. Top panel 54 has a thickness of approximately 1.9 mm. Lower panel 53 has a thickness of approximately 6.35 mm. Shell 58 is formed so that two rows of openings 69 extend through lower panel 53. Each row of openings 69 contains 4 openings. Shell 58 is further shaped so as to have a step 102 within panels 51-54 that is recessed relative to the outer rim of shell. Here, the outer rim is the coplanar faces of the panels 51-54 (rim not identified) that are directed towards lid 60. Step 102 extends circumferentially around the shell 58 and is recessed inwardly relative to the rim. The step 102 is spaced inwardly away from the outer edge of the shell rim. Sections of step 102, it should therefore be appreciated, are formed in each one of the panels 51-54.

Figure 6:
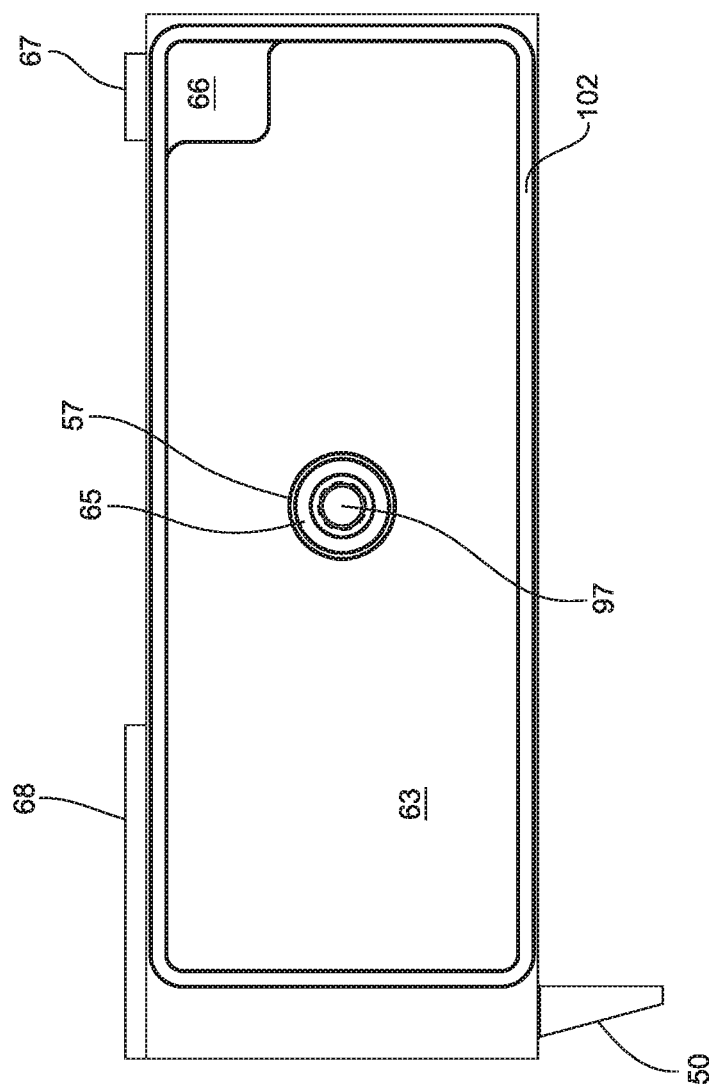
FIG. 6 is a plan view of the control module shell without lid illustrating the step for the outer O-ring and the post for the inner O-ring.
Figure 6A:
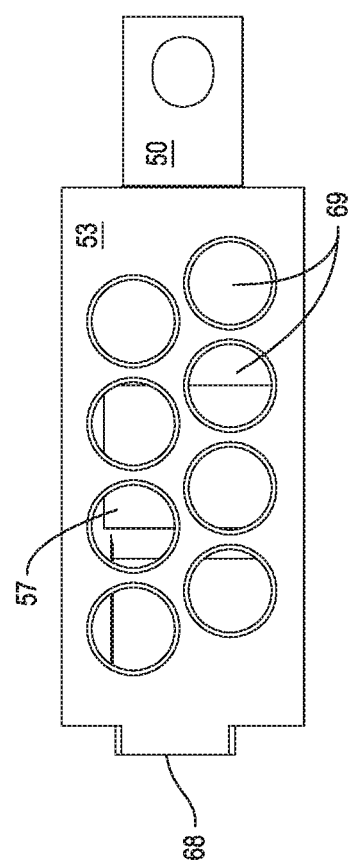
FIG. 6A is a plan view of the lower panel of the control module illustrating the bore holes that accept the seal assembly

A post 57 is formed integrally with and extends outwardly from shell base panel 63. Post 57 extends away from the inner face of base panel 63 toward lid 60. Post 57 is cylindrical in shape. The post has a height less than that of panels 51-54. The post 57 is formed to have a closed end threaded bore 97, as shown in FIG. 17, which extends inwardly from the outer circular face of the post (bore face not identified). Post 57 is further formed so as to have an annular groove 65, as seen in FIGS. 6 & 17, which extends inwardly from the face of the post. Groove 65 is thus located inwardly of the outer circular wall of the post 57 and outwardly of the inner surface of the post that defines bore 97. In another embodiment of this invention, plural posts 57 are formally integrated with and extend outwardly from shell base panel 63.

Located internal to and formed integrally with shell 58 is a block 66. Block 66 is located inside the shell 58 in the corner where side panel 52 and top panel 54 meet. Shell 58 is formed so that the block 66 extends outwardly from the inner face of the base panel 63. The height of the block 66 is less than the coequal height of the panels 51-54. Two keys 67 and 68 extend distally forward from the outer face of shell side panel 52. Key 67 is circular in shape. Key 68 is rectangular in shape. As seen in FIG. 6, key 67 extends over side panel 52 from a location spaced from top panel 54. Key 67 extends essentially outwardly from the outer face of the side panel 52 that is directly opposite the section of the inner face of the panel 52 against which block 66 abuts. The shell 58 is further formed so that a closed-ended threaded bore 43 (seen in phantom in FIG. 17), extends inwardly from the exposed face of key 67, through the adjacent section of side panel 52 and into block 66. Key 68 extends from the end of the side panel 51 that forms a corner edge with bottom panel 53. Key 68 extends along the side panel 52 a distance equal to approximately one-quarter the total length of the panel.

Control module shell 58 is also formed to have a tab 50. Tab 50 extends away from the outer face of side panel 51. Tab 50 is located immediately above the bottom edge of panel 51, above lower panel 53. Tab 50 is formed with a triangular shape from the top view. In the illustrated version of the invention, tab 50 is generally in the form of a right-angle triangle wherein the hypotenuse extends upwardly and outwardly away from the shell bottom panel 51. The tab 50 is formed so that in the outmost section there is a through opening (not identified).

Figure 7:
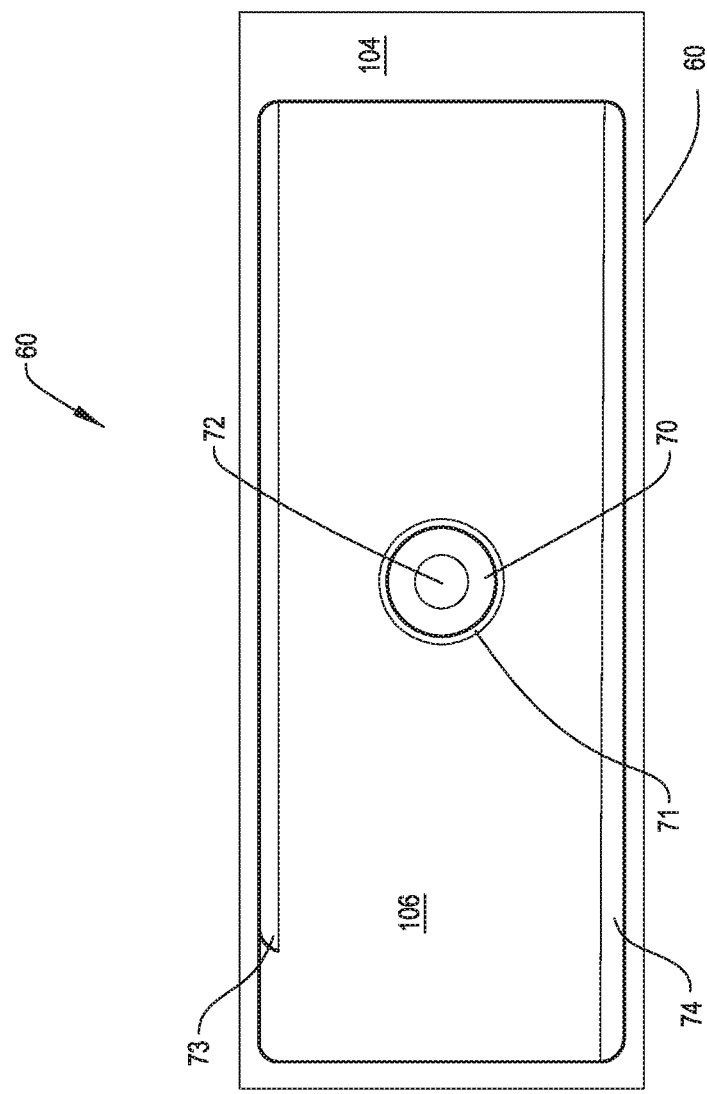
FIG. 7 is a plan view of the bottom of the control module lid.

As shown in FIGS. 5 and 7, lid 60 is formed as a single-piece unit and is shaped to have a panel 106. Panel 106 is in the form of a rectangle with rounded corners. The panel 106 is dimensioned to slip fit in the void space defined by shell panels 51-54. Two ribs 73 and 74 are formed integrally with the panel 106. Ribs 73 and 74 extend downwardly from the opposed longitudinal edges of the panel 106. Each rib 73 and 74 extends longitudinally along the panel 106. Each rib 73 and 74 is located inwardly of one of the longitudinal edges of the panel 106. Rib 73 is slightly shorter in length than rib 74. The difference in rib length is so that, when the lid is seated over the shell 58, the truncated end of rib 73 can seat next to shell block 66.

Lid 60 is further formed to have a rim 104 that projects outwardly from panel 106. Rim 104 extends outwardly around the outer perimeter of the panel 106 and extends circumferentially around the panel 106. The added length and width of rim 104 provides lid 60 with a length and width equal to the corresponding dimensions of the shell 58. The outer surface of rim 104 is coplanar with the outer surface of the lid panel 106. The thickness of the rim 104 is less than that of panel 106. Consequently, on the inner side of the lid 60 here is a step (not identified) between the inner surface of the rim 104 and the inner surface of panel 106.

A cylindrical boss 70 also extends downwardly from lid panel 106. Boss 70 is positioned so that, when the lid 60 is disposed over shell 58, the boss 70 is aligned with the underlying shell post 57. Boss 70 has a diameter slightly greater than that of shell post 57. Boss 70 is formed to have an inner face that has a lip 71 that extends downwardly, towards shell base panel 63. Lip 71 extends circumferentially around the outer perimeter of the inner face of the boss 70. Lip 71 which is ring-like in shape, has an inner diameter that facilitates the tight slip fitting of the lip 71 around shell post 57. Lid 60 is further formed so that a bore 72 extends axially through boss 70 and the overlying section of lid panel 106. Lid panel 106 has a tapered counterbore 108 that extends inwardly towards and is centered around bore 72.

O-rings 61 and 62 are made from rubber/plastic such as fluoroelastomers. The material from which the O-rings 61 and 62 are formed must be able to withstand exposure to temperatures of at least 135° C. without breaking down. One such material is a fluoroelastomer manufactured by Seals Eastern, Inc. and sold under the trademark AFLAS. Both O-rings 61 and 62 are circular in cross-section.

Inner O-ring 62 is circular in shape and is dimensioned to fit in groove 65 formed in the exposed face of shell post 57. The outer diameter of O-ring 62 is such that it extends approximately 0.25 mm above post 57.

Outer O-ring 61 is rectangular in shape and designed to seat over shell step 102. O-ring 61 is designed to extend above the outer rim of shell 58 by the same distance as O-ring 62 extends above post 57.

FIGS. 8 and 10-14 show the components of seal assembly 56. Specifically, the assembly includes a number of active seals 79. Each active seal 79 extends between one of the pins and the circular inner wall of the shell lower panel 53 that defines the opening 69 through which the pin extends. An outer retaining cap 76 is press fitted into openings 69 of the lower panel 53. Outer retaining cap 76 is pressed over pins 75. An inner retaining cap 77, also part of the seal assembly, is press fitted into openings 69 of the lower panel 53. Retaining caps 76 and 77 hold active seals 79 in openings 69. In one version of this invention, active seal 79 is a polyimide energized seal.

Figure 11:
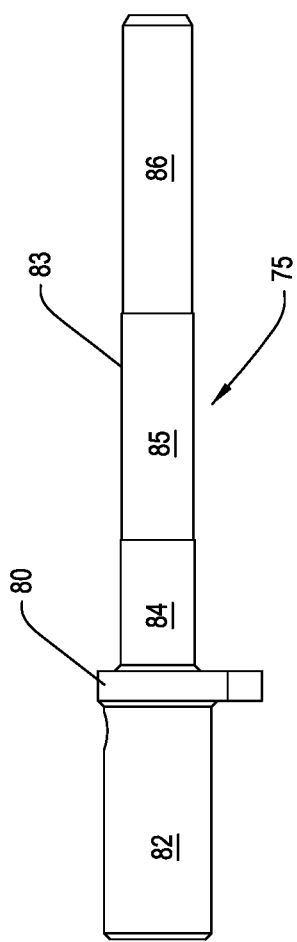
FIG. 11 is a side view of the pin illustrating the separate sections of varying diameter along the long axis of the pin shaft, and the D-shaped pin collar.
Figure 12:
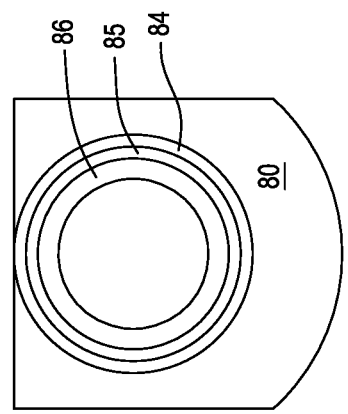
FIG. 12 is a plan view of the back of the pin illustrating the D-shaped pin collar.

FIGS. 11 and 12 illustrate the pin 75 over which electrical signals are conducted between the internal components of the control module 40 and the external components. Each pin 75 has a D-shaped collar 80, a head 82, and a shaft 83. The collar 80 projects radially beyond the end of the shaft 83. The head 82 has a closed-end bore 110. The shaft 83 is comprised of three sections of decreasing diameter. There is a first portion 84, the largest diameter section that extends inwardly from collar 80. A second portion 85 extends inwardly from the first portion 84. A third portion 86 extends inwardly from the second portion 85. The first portion 84 has a diameter that is larger than the diameter of the second portion 85. The second portion 85 has a diameter that is larger than the diameter of third portion 86.

In the described version of the invention module 40 has eight pins 75. Two pins 75 are connected to the tool power source. One pin 75 each is connected to each of the three phase windings internal to the tool motor 34. The remaining three pins 75 serve as conductive members over which control and tool status signals are exchanged between the components inside the module 40 and those outside the module. Each pin 75 extends through a separate one of the shell bores 69. In one embodiment of the invention, at least one pin is used to generate the electrical connection to components internal to module shell 58.

Figure 13A:
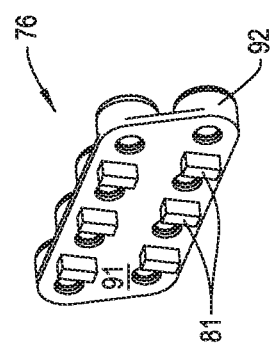
FIG. 13A is a perspective view of the outer retaining cap.
Figure 13C:
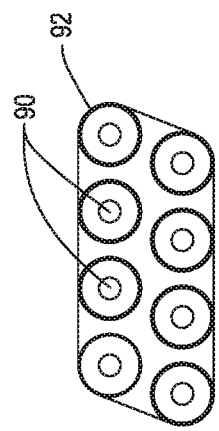
FIG. 13C is a plan view of the inwardly directed face of the outer retaining cap.
Figure 13B:
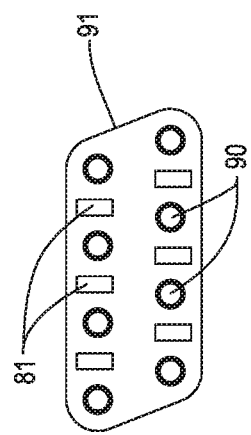
FIG. 13B is a plan view of the outwardly directed face of the outer retaining cap.
Figure 15:
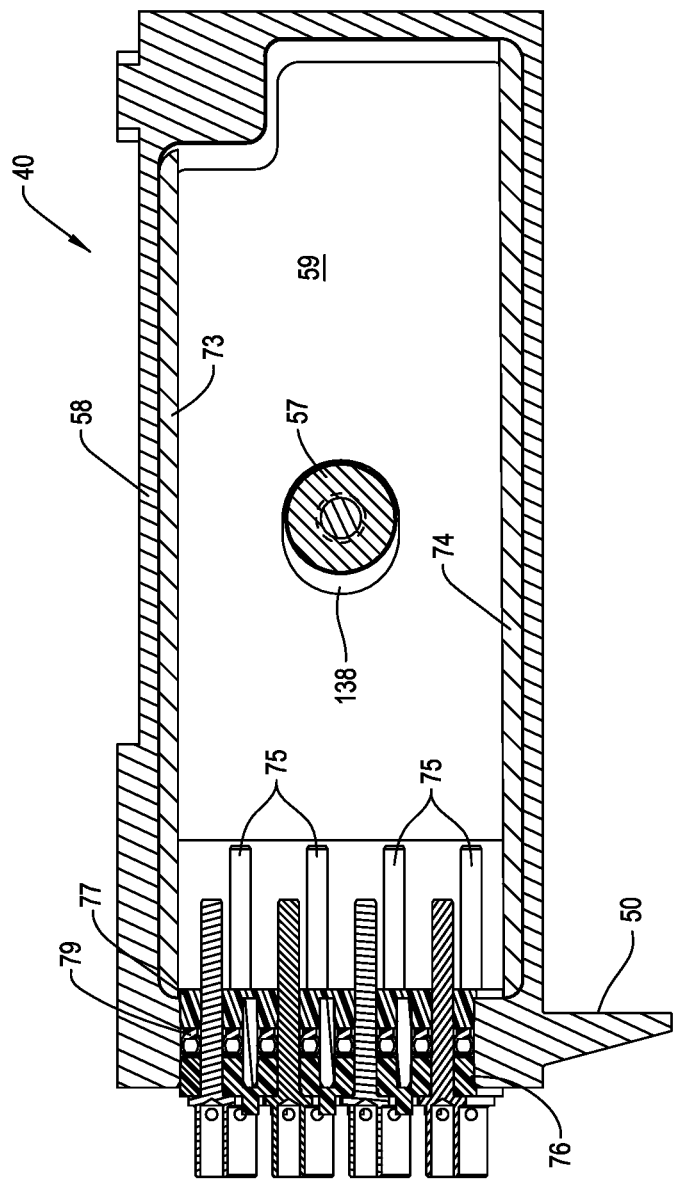
FIG. 15 is a cross sectional view of the control module illustrating the module shell together with the finished seal assembly inserted within the module shell, the seal assembly illustrating each pin, active seal, outer retaining cap and inner retaining cap.
Figure 16:
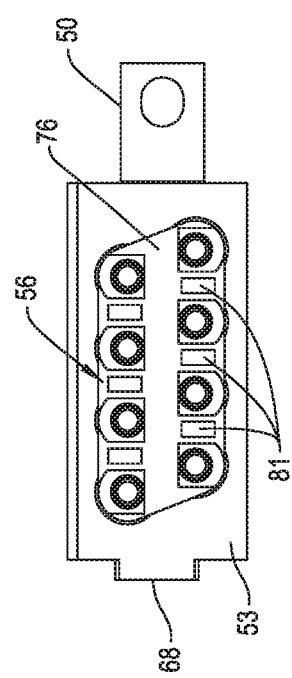
FIG. 16 is a plan view of the lower panel of the control module illustrating the finished seal assembly within the module shell.

Shown in FIG. 13 is the parallelogram-shaped outer retaining cap, 76. Outer retaining cap 76 of FIG. 13 has a parallelogram-shaped outer cap plate 91 with rounded corners (not identified). A plurality of cap bosses 92, equal to the number of shell lower panel openings 69 extend inwardly from the inwardly directed face of plate 91, the face directed towards shell 58. Bosses 92 have a diameter that facilitates the press fit of the bosses 92 in the shell openings 69. A bore 90 extends axially through the boss 92 and the section of the plate 91 from which the bore projects. Bore 90 has a diameter that is a press fit relative to the diameter of pin shaft first portion 84. Rectangularly shaped tabs 81 extend outwardly from the outwardly directed face of the outer cap plate 91. Six tabs 81 extend outwardly from outer plate 91. Where two tabs 81 are located on either side of bore 92 the tabs are spaced apart a distance slightly greater than the distance between the opposed parallel sides of a pin collar 80. When the control module 40 is assembled pin collars 80 are located adjacent to the tabs 81. The tabs 81 thus inhibit the rotational movement of the pins 75.

Shown in FIG. 14 is the parallelogram-shaped inner retaining cap 77. Inner retaining cap 77 of FIG. 14 has a parallelogram-shaped inner cap plate 93 with rounded corners (not identified). A plurality of cap bosses 94, equal to the number of shell lower panel openings 69 extend outwardly from the outwardly directed face of plate 93, the face directed into shell 58. Bosses 94 have a diameter that facilitates the press fit of the bosses 94 in the shell openings 69. An inner cap bore 95 extends axially through the cap boss 94 and the section of the plate 93 from which the bore projects. Bore 95 has a diameter that is a press fit relative to the diameter of pin shaft second portion 85. Pin shaft third section 86 is slip fit through the entire seal assembly 56.

Figure 18:
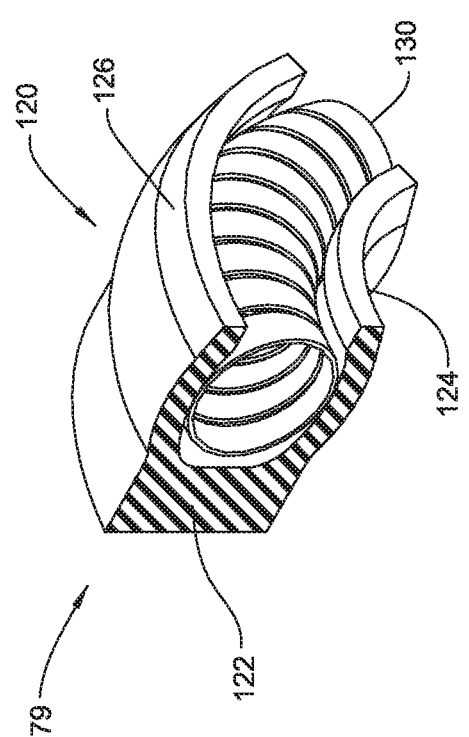
FIG. 18 is a sectional view of an active seal illustrating a boot, and a spring disposed within the boot.

Each active seal 79, one seen in FIG. 18, includes a boot 120 and a spring 130. Boot 120 is formed from PTFE sold under the trademark Teflon or another material that has both some degree of flexibility and capability of withstanding the rigors of autoclave sterilization. The boot 120 must also be able to not melt when exposed to the heat associated with soldering wires to pins 75. The boot 120 is generally ring-like in shape. The boot 120 has a base 122 that, in cross section, appears rectangularly shaped. Two spaced apart, ring-shaped skirts 124 and 126 extend away from the opposed inner and outer sections of the base 122. Both skirts 124 and 126 extend generally away from the outwardly directed face of boot base 122. Skirt 124, the inner skirt, also extends slightly radially inwardly from the inner annular face of the base 122. Skirt 126, the outer skirt, extends slightly radially outwardly from the outer annular face of the base 122.

Owing to the spacing apart of the skirts 124 and 126, there is an annular gap (not identified) above the base 122, between the skirts 124 and 126.

Spring 130 is formed from a nickel-chromium-based alloy sold under the trademark Inconel. This material, like boot 120, is capable of withstanding the sterilization of tool 30. The metal forming spring 130 is helically wound. Spring 130 is seated in the annular gap between the boot skirts 124 and 126. The spring 130 has a diameter that is greater than the width across the gap between the skirts. For example, if this gap has a relaxed width of 1.0 mm, the spring has a diameter of 1.1 mm. In alternative versions of the invention, spring 130 may be replaced with a biasing member that replicates the biasing force of spring 130.

Spring 130 imposes a biasing force on the skirts that cause inner skirt 124 to bow inwardly, toward the center of the boot 120, and outer skirt 126 to bow outwardly, away from the center of the boot. Collectively, boot 120 and spring 130 are selected so that, when the active seal is assembled, the distance between the outer surfaces of the boot skirt 124 and 126 is greater than the annular gap present between the section of the pin 75 disposed in the shell bore 69 and the adjacent bore-defining inner surface of the shell 58. In the described version of the invention, the active seal is disposed around the pin stem second portion 85. Inner skirt 124 presses against this pin portion. Outer skirt 126 presses against the surrounding annular wall of the shell 58 that defines bore 69. This portion of the pin 75 has a diameter of approximately 1.530 mm. Shell bore 69 has a diameter of approximately 4.43 mm. The distance across the bowed boot skirts 124 and 126 is approximately 1.46 mm.

Printed circuit board 59 contains the components 140 used to regulate the application of power to the tool power generating unit, motor 34. The exact structure of the components 140 is a function of the power generating unit integral with the tool. Therefore, the structure of these components is not material to this invention. When the power generating unit is a motor, the circuit described in the incorporated by reference U.S. Pat. No. 7,638,958 may be built onto circuit board 59. These components include first and second sets of sensors (not illustrated). The first set of sensors monitor the actuation of the trigger switches 46 and 47. The second set of sensors monitors the state of the tool motor. To facilitate the responsiveness of the sensors, portions of the shell 58 may be formed from material through which the physical quantity (quantities) monitored by the sensors can pass. For example, if one or more of the sensors monitors a magnetic field (fields) adjacent sections of the shell may be formed from combinations of magnetic and non-magnetic material that focuses the field (fields). If the sensors monitor photonic energy (light) the shell 58 may have panels or sections of panels that are transparent to the wavelength of the monitored light.

Printed circuit board 59 is formed with an opening 138. When the circuit board 59 is seated in the housing shell 58, the shell post 57 extends through opening 138.

Figure 8:
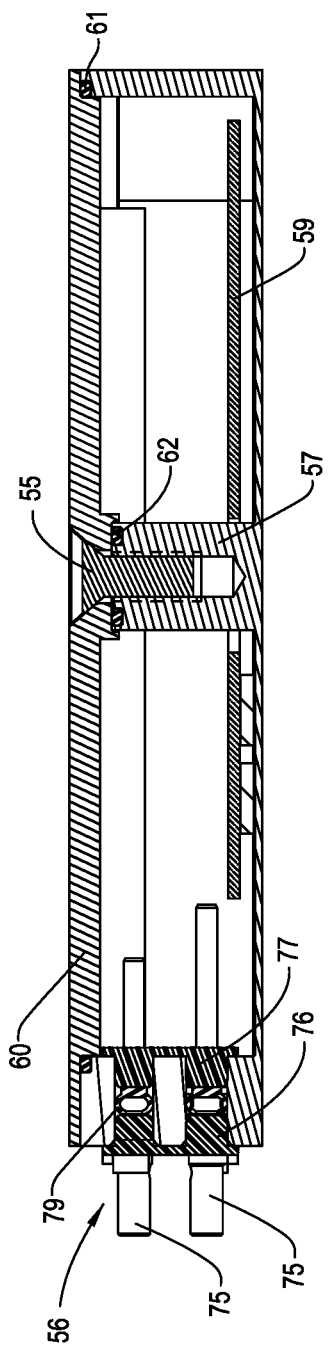
FIG. 8 is a cross sectional view along the long axis of the control module illustrating the control module lid and shell, fastener, pins, outer retaining cap, inner retaining cap and active seals.
Figure 9:
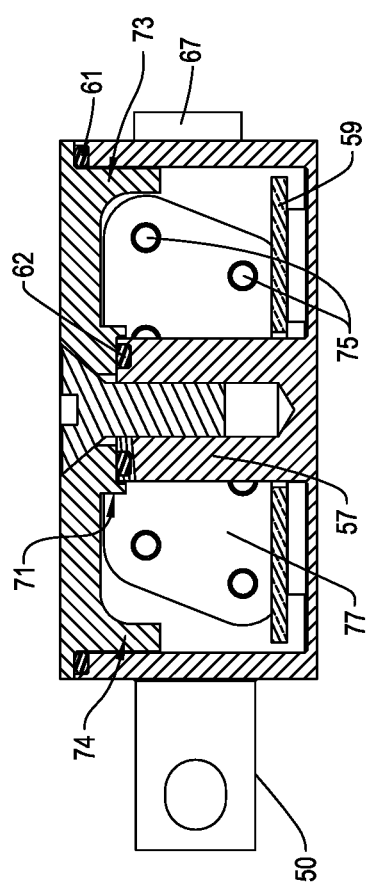
FIG. 9 is a cross sectional view across the short axis of the control module illustrating the control module lid fastened to the shell using a fastener.

Control module 40 is first assembled by press fitting pins 75 into cap bores 90 of outer retaining cap 76. More particularly, the pin stem first portions 84 are press fit in cap bores 90 so that the remaining portions of the pin stems extend out through bosses 92. Active seals 79 are then inserted over the pin stem second portions 85. Outer retaining cap 76 is then press fit to the lower panel 53 of shell 58 so that bosses 92 seat in shell bores 69. Each active seal 79 is fitted in the associated shell bore 69 so that, as seen in FIG. 8, the free ends of the boot skirts 124 and 126 are directed towards the adjacent outer retainer cap boss 92. When each seal is so positioned, the spring 130 simultaneously causes boot skirt 124 to press against the pin stem second portion 85 and boot skirt 126 to press against the inner circular wall of the shell 58 that defines the bore 69. Each seal 79 thus functions as a substantially gas-tight seal between each pin 75 and the surrounding portion of the shell bore 69.

The inner retainer cap 77 is then fit over the inner face of the shell lower panel 53 and the pins 75. Owing to the relative dimension of the pins 75 and boss bores 95, the cap bosses 94 initially are slip fit over the pin third shaft section 86. Then, the cap bosses 94 are simultaneously press fit into the lower panel openings 69 and over the pin second shaft section 85. The components forming seal assembly 56 are further configured, so that when assembled, the active seals 79 are not compressed between the opposed cap bosses 92 and 94. Instead, even with seals 79 disposed in a bore 69, there is space within each shell bore 69 for the active seal 79 to move between the cap bosses 92 and 94. In the described version of the invention, wherein the shell bore 69 has a length of 6.35 mm and a diameter of 4.43 mm, this distance is approximately 1.91 mm. When the seal assembly 56 is mounted to the shell 58, the pin third portions 86 extend beyond inner cap plate 93 into the shell 58.

Once seal assembly 56 is mounted to shell 58, circuit board 59 is fitted on top of base panel 63 of module shell 58. In the described version of the invention, the circuit board 59 is fit below the two rows of pins. Contacts on the circuit board 59, not illustrated and not part of this invention, establish mechanical and conductive connections between the bottom row of pins 75. Pins 75 create mechanical and conductive connections between the exposed pin portions 86 adjacent the top of the board and the components on the board. Solder and wire connections, not illustrated and not part of this invention, may be used to establish conductive paths between the pins 75 that extend over the circuit board 59 and the complementary board components.

Fasteners or adhesive, not illustrated and not part of this invention, are used to hold the circuit board in the shell 58.

Once the circuit board 59 is in place, assembly of the control module is completed by the securement of the lid 60 to the shell 58. This process starts with the seating of O-ring 61 over module step 102. O-ring 62 is seated in the post groove 65. Lid 60 is then fitted over the open end of shell 58. Owing to the dimensioning of the components, there is a close slip fit between the outer surface of each lid rib 73 and 74 and the inner surface of, respectively, the adjacent side panel 52 and 51. The clearance between each rib 73 and 74 and adjacent side panel may be approximately 0.05 mm. As a consequence of the fitting of the lid 60 over the shell, the lid boss 70 seats over shell post 57. More particularly, lip 71 integral with lid boss 70 is fit around the outer perimeter of the post 57.

Fastener 55 is then used to secure the lid 60 to the shell 58. Fastener 55 is also secured to the lid 60 with an adhesive manufactured by the Henkel Company and sold under the trademark Loctite. The fastener is inserted through lid bore 72 and threaded into shell post bore 97. When tightened, the fastener 55 presses the lid 60 against the shell 58. As a result of this movement, O-ring 61 is compressed between the shell step 102 and the lid rim 104. O-ring 62 is compressed between the shell post groove 65 and the face of lid boss 70 so that lid boss 70 provides a face seal. As a consequence of the compression of the O-rings 61 and 62, the O-rings form substantially gas-tight seals between the module housing-forming shell 58 and lid 60.

Figure 10:
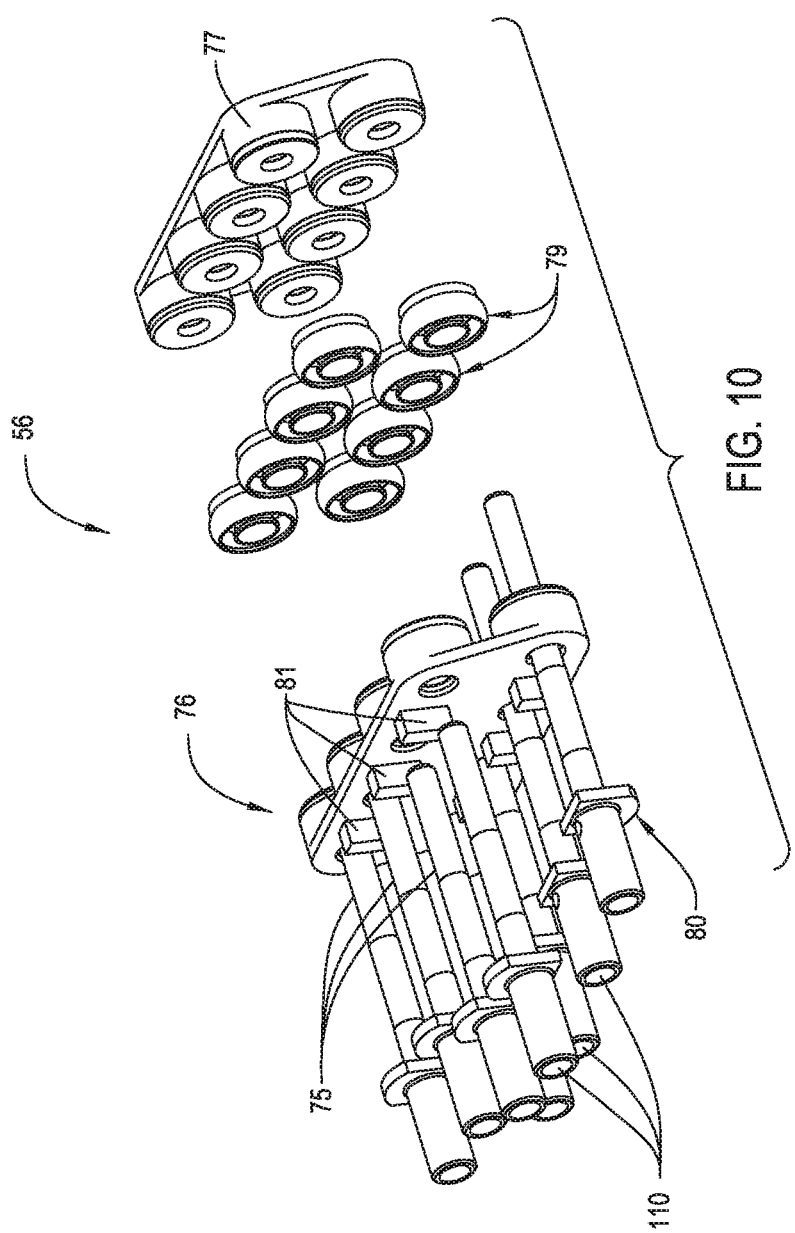
FIG. 10 is an exploded view of the seal assembly illustrating the pins, the outer retaining cap, the active seals, and inner retaining cap.

The assembled control module 40 is then inserted into handle void space 29. Keys 67 and 68 serve as spacers to ensure the control module 40 is properly positioned in the handle 38. Key 68 also serves to transfer heat generated by the internal electrical components of control module 40. Heat dissipated from the shell 58 transfers through key 68 and into the handle 38. Fasteners, not illustrated, hold the control module 40 to the handle 38. One fastener extends through closed-ended threaded bore 43 of key 67 into block 66 to anchor module 40 to the handle 38. A second fastener extends through the opening in tab 50 to an adjacent structural member internal to the tool handle 38. Tab 50 is angled to force control module 40 into the handle 38. Once the control module 40 is secured to the rest of the tool 30, the appropriate conductors (not illustrated) are attached to the exposed pin heads 82. Each conductor is solder secured into the closed-end bores 110 internal to the pin head 82, as shown in FIG. 10.

Once the tool 30 is completely assembled, the tool is ready for use. The tool is used like a conventional tool. A medical practitioner depresses one of the trigger switches 46 or 47. This motion is detected by the circuit internal to module 40. The circuit then causes the appropriate energization signals to be applied to the motor 34. This results in the cutting accessory being actuated in order to perform the desired medical/surgical procedure.

Once tool 30 is used, the tool can be autoclave sterilized like a conventional tool. In this process, the tool is placed in a sealed chamber into which saturated steam is introduced at temperatures up to 135° C. and pressures as high as 305,000 Pa absolute. During this process, the highly pressured steam presses against the outside of the module housing. A 686 mm of Mercury vacuum is then drawn on the handpiece. The seal-forming O-rings 61 and 62 prevent essentially any leakage of the highly pressurized steam into the control module 40. During the steam pressurization cycle, the pressurized steam presses inwardly on the structural members of the module housing, shell panels 51-54 and 63, and lid 60. The differential pressures between the inside and outside of the module housing results in the inward flexing of the housing panels, especially the lid 60 and the shell base panel 63. This inward flexing of the lid 60 is opposed by the abutment of the shell post 57 against the lid. During the vacuum drawing cycle, the differential pressure results in the outward flexing of the panels forming the housing. This outward flexing of the lid 60 is opposed by the ribs 73 and 74 and the fastener 55. The inhibiting of this outward flexing of the shell 58 and the lid 60 reduces the displacement of the lid 60 away from outer O-ring 61 and the breaking of the seal established by the lid-against O-ring contact.

During sterilization, the seals 79 function as substantially gas-tight barriers between the bore 69 defining walls of the shell lower panel 53 and pins 75. It should be appreciated that during the sterilization process, the module shell 58 and pins 75 undergo some thermal expansion. Thermal coefficients of expansion of the materials forming module shell 58 and pins 75 are different. Pin 75 has a lower thermal coefficient of expansion than the surrounding shell 58. Consequently, there is an increase in the width of the annular gap between each pin 75 and surrounding shell wall. In response to this change, each seal spring 130 pushes the adjacent boot skirts 124 and 126 outwardly away from each other. Thus, each seal 79 maintains the barrier between the shell 58 and associated pin 75 during this portion of the autoclave process. Also during this portion of the autoclave process, a fraction of the pressurized steam may flow into the annular space between each pair of seal skirts 124 and 126. This pressurized steam thus functions as a second force that pushes the skirts 124 and 126 outwardly away from each other so as to further enhance the tightness of the substantially gas-tight seal.

Even with this deformation of the boot 120, skirt 124 still abuts pin 75 and skirt 126 still abuts the surrounding inner wall of the shell lower panel 53. Each seal 79 therefore maintains a barrier around the pin 75 over which the seal is seated. Further, this deformation of the seal also means that thermal expansion of the shell 58 and pin 75 are not opposed by any forces that could impose fracture-inducing stresses on these components.

During this process, the outward pushing of the seal skirts 124 and 126 away from each other causes a lengthening of the skirts. The skirts are able to expand into the clearance space in the bore 69 between cap bosses 92 and 94. This ability of the skirts 124 and 126 to freely expand allows the boots 120 to maintain their integrity.

Once tool 30 is sterilized, the tool is removed from the autoclave. The temperature of the tool returns back to ambient levels. At this time, shell 58 and pins 75 undergo thermal contraction. In response to the decreasing in size of these components, the width of the annular gap between each pin 75 and the surrounding shell wall decreases. This causes a like decrease in the distance between the boot skirts 124 and 126. Each spring 130 is therefore subject to some radial compression. Owing to their flexible nature, springs 130 are able to undergo this compression without plastically mechanically deforming. Consequently, each spring 130 is still able to impose force on the associated boot that holds the skirts 124 and 126 away from each other. Springs 130 are thus able to supply the forces needed to maintain seals around pins 75 as the tool is, over time, subjected to plural autoclave sterilizations.

Tool 30 of this invention has a control module with sets of seals able to withstand the rigors of repeated autoclave sterilization. O-rings 61 and 62 stop steam from entering between the module 40 between the shell 58 and lid 60. Due to the same material used in forming shell 58 and lid 60, creating equal coefficients of thermal expansion, O-rings are able to be used. Seal assembly 56 blocks steam from entering the control module 40 through shell bores 69. Both these sets of seals are relatively economical to provide.

Further, shell 58 and lid 60 have features, shell post 57 and lid ribs 73 and 74 that inhibit the flexing of the control module housing when the tool 30 is pressurized during sterilization. By increasing the stiffness of the lid 60, the risk of having the seal broken is reduced.

Another benefit of tool 30 of this invention over a tool with a control module that is brazed or welded closed is that it is possible to easily open module 40. This is accomplished by unscrewing fastener 55 and then removing lid 60. Thus, one could periodically remove the lid 60 from the shell 58. This process can be performed in a very dry (low humidity) work environment in order to facilitate the evaporation of any water that may have worked itself into the module housing. The components internal to the module can be inspected to determine if there is any evidence of potentially failure-inducing corrosion. Prior to resecuring of the lid 60 to the shell 58, the housing can be provided with new O-rings 61 and 62. Thus, unlike some present control modules, the control module of this invention is designed to allow preventive maintenance and repair. This can avoid the more costly process of having to periodically provide the tool with a completely new control module.

II. Alternative Embodiments

The above description is directed to one version of the invention. Other versions of the invention may have features different from what has been described.

For example, there is no requirement that all versions of the invention contain both the described seal assembly 56 and O-rings 61 and 62. Other versions of this invention may only have a single one of the features.

In some versions of the invention, the O-rings 61 and/or 62 may be replaced with an active seal similar to active seal 79. Each active seal would have a boot sized to fit between where the cover and lid would otherwise abut. Internal to the boot is one or more biasing components similar to seal spring 130 that exert a force on the boot skirts. These active seals would be similar in shape and size to the O-rings 61 and 62. These active seals would provide the function of the active seal 79 in the location of current O-rings 61 and 62. In other versions of the invention, O-rings 61 and/or 62 may be replaced with a gasket or a material similarly capable of establishing a substantially gas-tight seal between the structural members of the control module. The seal function performed by both O-rings 61 and 62 may be performed by a single piece of an elastomeric material. This piece of elastomeric material is positioned so as to extend between both the shell rim-to-lid interface and the post-to-lid interface.

In these as well as other embodiments of the invention, it may not be necessary to provide the module shell with an inwardly directed step against which the rim-to-lid seal seats. Thus, in these versions of the invention, the rim-to-lid seal may directly abut the outer most face of the shell rim.

In alternative versions of the invention, components other than the cap bosses may serves as the stops that prevent longitudinal movement of the active seals out of the module panel in which they are seated. There is no requirement that a plurality of cap bosses for either the inner retaining cap or outer retaining cap extend from a common plate. In these versions of the invention, associated with each active seal, are an inner stop and an outer stop. Neither of these stops are connected to any of the other stops that may be fitted to the common module panel. This is especially true in versions of the invention in which the conductive pins that extend through the control module are either widely spaced apart from each other (0.5 cm or more) or extend through different panels in the control module.

Figure 18A:
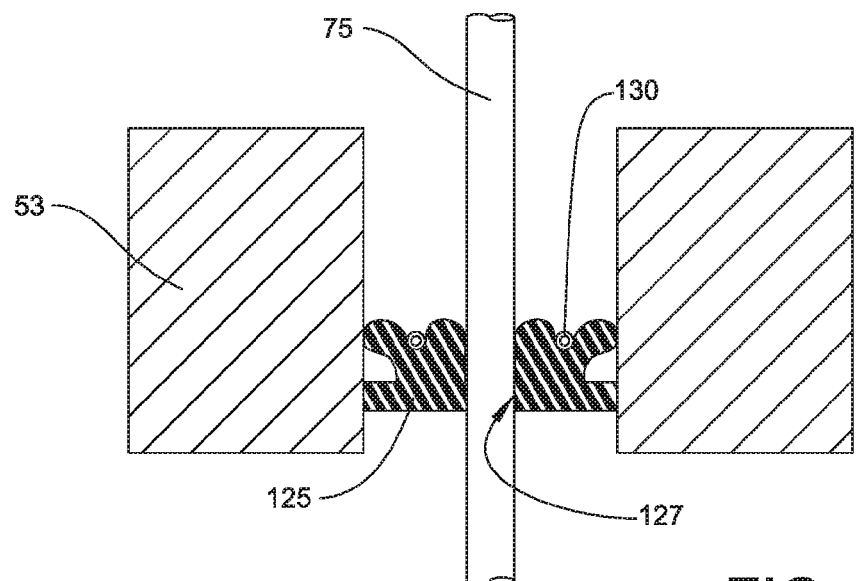
FIG. 18A is a sectional of view of an alternative embodiment of the seal assembly illustrating a stop integral with the active seal, and a spring disposed within the seal boot.

Further, this invention is not limited to seal assemblies wherein the stops are rigid cylindrical members that are simply pressed into the panel opening in which they are seated. One such alternative stop 125, now described by reference to FIG. 18A. First stop 125 and active seal 127 are a single piece of rubber. Stop 125 may be integrally formed as a portion of the active seal 127 so as to tightly fit against the bore defining inner wall of lower panel 53. First stop 125 is a circumferential step or ring located inwardly from the bore defining inner wall of lower panel 53. Stop 125 and seal 127 are disposed around a conductive pin 75. A spring 130 is disposed between the seal boot skirts (not identified). Not illustrated in FIG. 18A is a second stop.

Figure 18B:
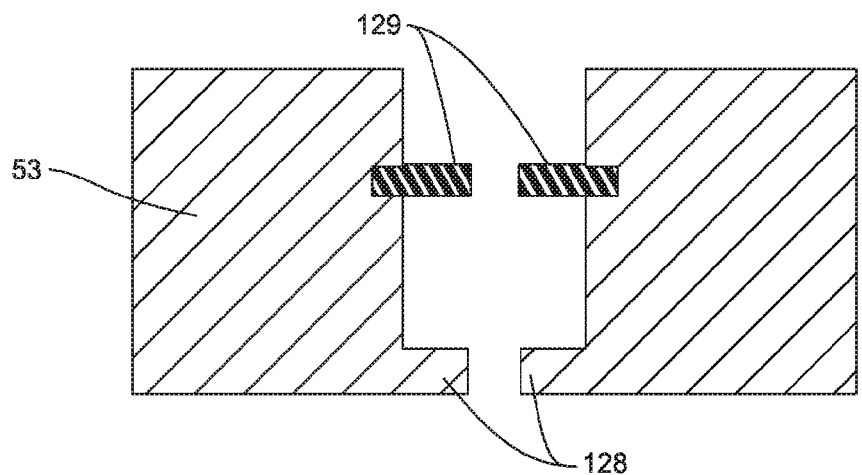
FIG. 18B is a sectional view of alternative stops that may be components of the seal assembly.

In alternative versions of the invention, a first stop 128 maybe integrally formed with the panel 53 itself, as shown in FIG. 18B. Stop 128 is comprised of the same material as panel 53. In these versions of the invention, the stop 128 consists of a circumferential ring or step that is part of the panel that extends inwardly into the bore defining inner wall of lower panel 53 in which the conductive pin 75 and active seal 79 are seated. This ring or step may be flush with either the outer or inner walls of the lower panel 53 and act as either an inner or outer stop. Alternatively, this ring or step may be recessed relative to the inner or outer wall of the lower panel 53. Not illustrated in FIG. 18B is the active seal 79 or conductive pin 75.

In some versions of the invention, a compression ring 129, as shown in FIG. 18B, may function as one, if not both, of the inner or outer stops. In these versions of the invention, the compression ring 129 forms the stop (or plug) function. It may be necessary to provide a panel 53 with an annular groove (not identified) that extends outwardly from the bore defining inner wall of lower panel 53. The outer perimeter or surface of the compression ring 129 seats or snaps into the annular groove.

These various alternative features may also be combined. For example, the compression ring or stop may be integrally formed with the active seal upon assembly of the module. The outer perimeter of the compression ring portion is snap fit into the groove formed in the bore defining inner wall of lower panel 53.

Likewise, in some versions of the invention, the features that inhibit rotation of the conductive pins may be formed with the inner stops.

Similarly, this invention is not limited to battery powered motorized surgical tools. In other versions of the invention, the tool that receives power over a cable connected to a control console. In other versions of the invention, the power generating unit may be a device that generates electrical energy, thermal energy or photonic energy. Other tools may generate other forms of mechanical energy, such as tools designed to vibrate the attached cutting accessory.

In other versions of the invention, the tool may not have the shell abutting post. Still other versions of the invention may have plural shell abutting posts. In these versions of the invention, less than all of the posts may be provided with features to facilitate the securement of the overlying lid to the post.

Similarly, there is no requirement that in all versions of the invention, the lid be provided with the two described stiffening ribs. In some versions of the invention, the lid may have only a single stiffening rib. Likewise in some versions of the invention, it may be desirable to provide the lid with three or more stiffening ribs. Similarly, there is no requirement that in all versions of the invention the ribs be simple linear structures. Other versions of the invention may have ribs with non-linear shapes.

Likewise, seal assembly 56 may have other constructions than what has been described. As mentioned above, the actual number of active seals is a function of the number of pins required to provide conductive paths to/from the control module. If there was no need to provide the module with pins to establish external communications links, fewer pins and companion seals are needed. A tool with sensors located outside of the control module may require more pins and, therefore, more seals. When a pin seal of this invention is provided there is no requirement that a single inner or outer retainer hold all the active seals 79 in place. In some versions of the invention, a pair of companion inner and outer retainers may hold a single active seal 79 in position.

Likewise, in some versions of the invention, the construction of the tool may necessitate that the pins that extend into the module housing be grouped together. In some versions of the invention, one set of pins may extend through a first one of the housing panels while a second set of pins extends through a separate housing panel. Thus, in this and other versions of the invention, a tool of this invention may have plural spaced apart seal assemblies 56, each of which includes one or more active seals.

Unless recited in the claims, the stated dimensions are for purposes of illustration only.

Likewise, while the module of this invention is designed for use with a surgical tool, its use is not limited to this type of tool. The module may be used to seal components contained in other devices. For example, the module can be used to seal components used in marine or aerospace environments. Further, the module may not only be used to house components used to regulate the operation of a tool. In alternative applications, the module of this invention may be used to house components used to perform functions other than those that control a power generating unit. For example, in one marine application, the module of this invention may be used for housing components used to process signals received/transmitted from a sonar transducer. Thus, it is an object of the appended claims to cover all such variations and modifications that come within the true spirit and scope of this invention.

Likewise, the sealed control module 40 of this invention may also be designed to facilitate the assembly of the module 40 and its internal components. In this version of the invention, seen in FIG. 19, a spacer 144 is attached on a surface of a control board 142, a printed circuit board. A mount 160 holds a plurality of Hall sensors 162, 164, 166 and 168 to the printed circuit board 142 within the module 40. Mount 160, along with spacer 144, align internal components in all three axes during and after manufacture.

In this version of the module 40, a printed circuit board 142 contains a plurality of analog Hall sensors 162, 164 and 166 used to regulate the application of power to the tool power generating unit, motor 34, or to be actuated by trigger switches 46, 47, now described by reference to FIGS. 1, 2 and 19. A sensor 168 is a digital Hall sensor. The position of analog Hall sensors 162, 164 is a function of the location of the power generating unit integral with the tool. When the power generating unit is a motor, the circuit described in the incorporated by reference U.S. Pat. No. 7,638,958 may be built onto circuit board 142.

Each analog sensor is comprised of a body (not identified) and a plurality of electrical leads (not identified) that extend away from the body. Analog sensors 162 and 164 facilitate regulation of the application of power to the motor rotor, 34. Sensor 164 has longer electrical leads than sensor 162 for manufacturing reasons. Each analog sensor 166 and digital Hall sensor 168 pair is used to regulate the application of power to the motor proportional to the position of an associated tool trigger switch 46 or 47. Applicant's Assignee's U.S. Pat. No. 7,638,958, incorporated herein by reference, discloses one analog Hall sensor/digital Hall sensor for powering the motor 34 or triggers 46, 47.

Figure 20:
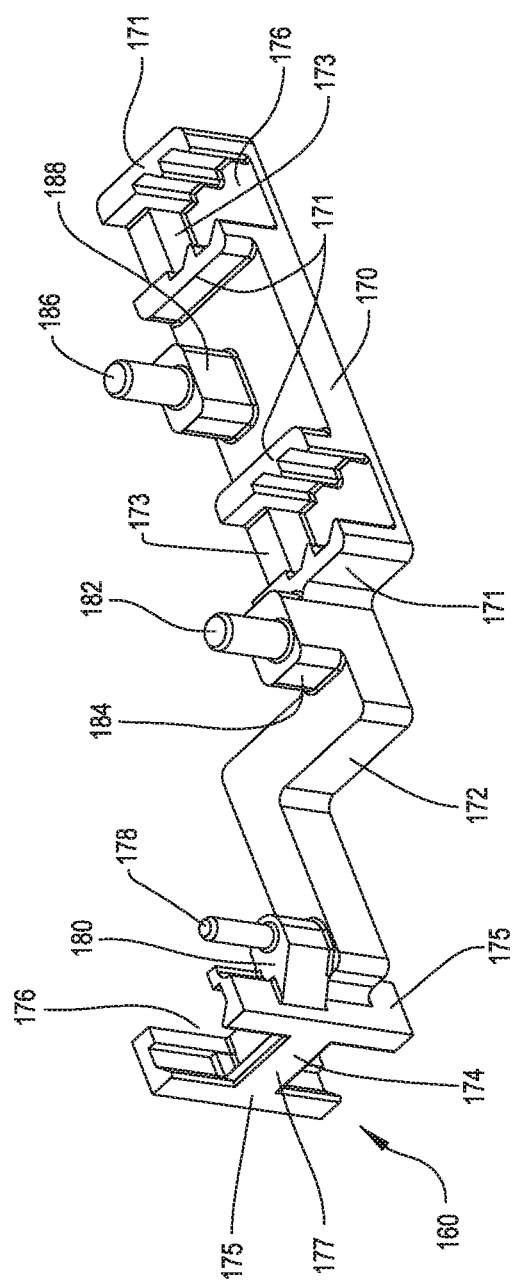
FIG. 20 is a perspective view of the mount.
Figure 21:
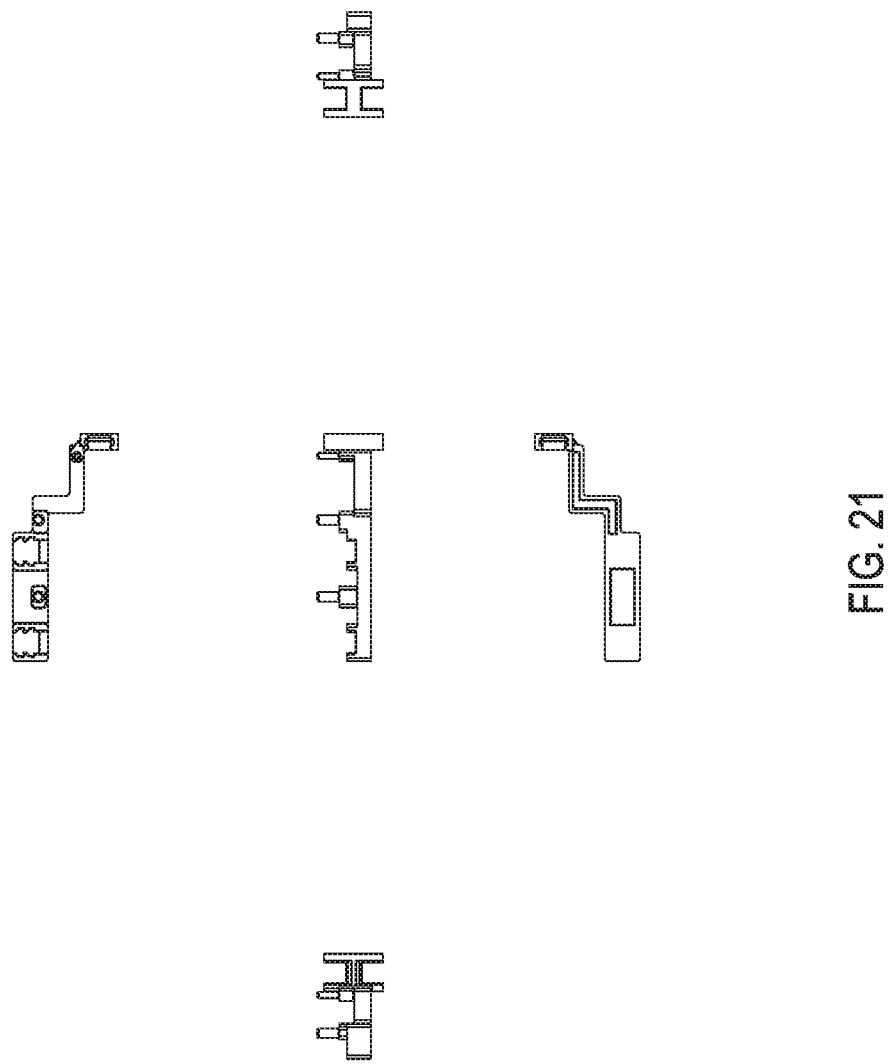
FIG. 21 is a plan view of the mount from the front, top, bottom and sides.

Mount 160 is comprised of a single piece of plastic. Mount 160 is comprised of three sections: a base 170, an L-shaped section 172, and a H-shaped section 174, now described by reference to FIGS. 20 and 21. Base 170 has opposed ends (not identified). On each end of base 170 is a pair of spaced apart side walls 171 defining a pair of slots 176. A connecting section 173 connects each side wall 171 with each an opposing side wall 171. Side walls 171 extend above the height of base 170. Side walls 171 are approximately equal in height. Each slot 176 is located forward of connecting section 173. On the top surface of base 170 is a pedestal 188. Pedestal 188 is rectangular in shape and extends from the surface of base 170. Pedestal 188 is located on the rear of the base 170 and equally spaced between opposed ends of base 170. Extending from a top surface of pedestal 188 is a post 186. Post 186 is circular in shape and has an approximate diameter of 1.4 mm. Connected adjacent to base 170 is the L-shaped section 172. L-shaped section 172 extends away from one end of base 170. L-shaped section 172 is attached to base 170 so as to be aligned with the adjacent connecting section 173. Located on one end of L-shaped section 172 is a pedestal 184. Pedestal 184 is rectangular in shape and extends from a top surface of L-shaped section 172. Pedestal 184 is approximately equal in cross-dimension to pedestal 188. Extending away from a top surface of pedestal 184 is a post 182. Post 182 is circular in shape and has a diameter equal to the diameter of post 186. Located on opposed end of L-shaped section 172 is a pedestal 180. Pedestal 180 is C-shaped and extends from the top surface of L-shaped section 172. Pedestal 180 is smaller in cross-dimension than pedestals 184 and 188. Extending away from a top surface of pedestal 180 is a post 178. Post 178 is smaller in diameter than posts 182 and 186. Connected adjacent to pedestal 180 of L-shaped section 172 is H-shaped section 174. H-shaped section 174 has a pair of opposed parallel spaced apart walls 175. Walls 175 comprise the opposed ends of H-shaped section 174. Connecting walls 175 is a cross-beam 177. Beam 177 is approximately linear with L-shaped section 172 and base 170. Walls 175 with beam 177 define a pair of slots 176. Each slot 176 is dimensioned to seat the body of an analog Hall sensor 162, 164 and 166 or the body of a digital Hall sensor 168, as shown by FIG. 19.

Pedestals 180, 184, and 188 extend to the same height above base 170 so as to form a plane to bottom out against a bottom surface of circuit board 142. Posts 178, 182 and 186 also extend to the same height above base 170 so as to form a plane.

Figure 22:
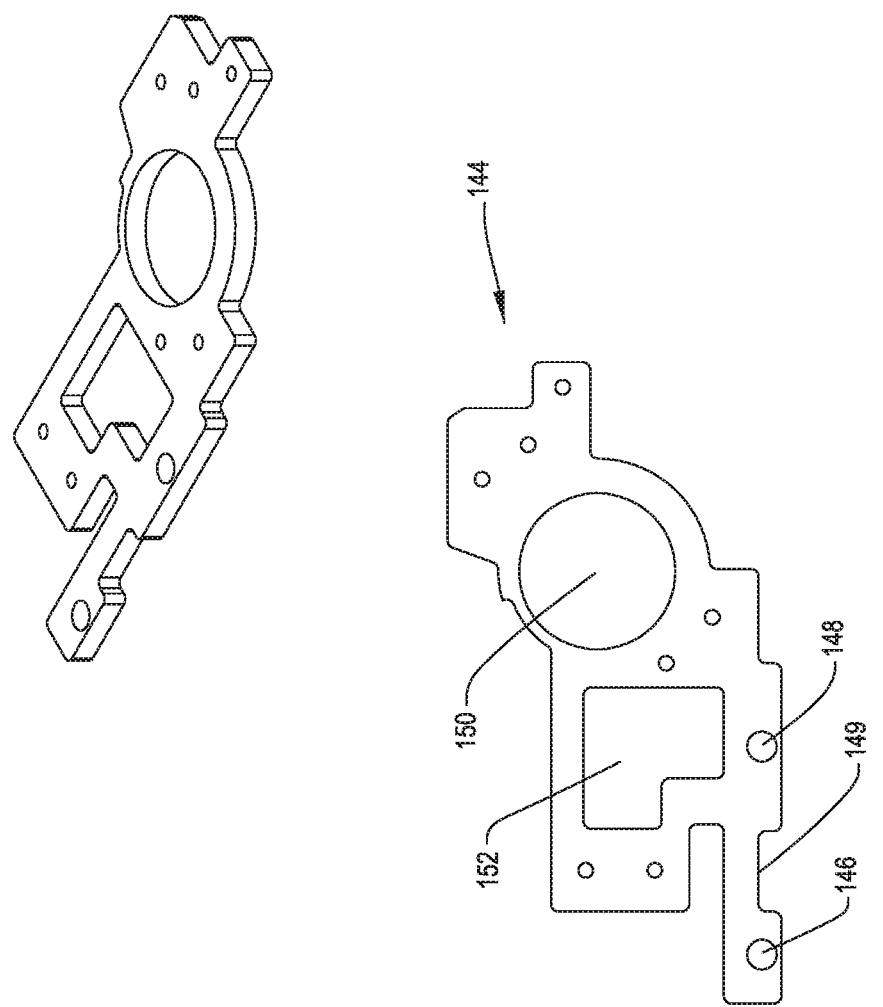
FIG. 22 is a plan view of the top of the spacer, and a perspective view of the spacer.
Figure 23:
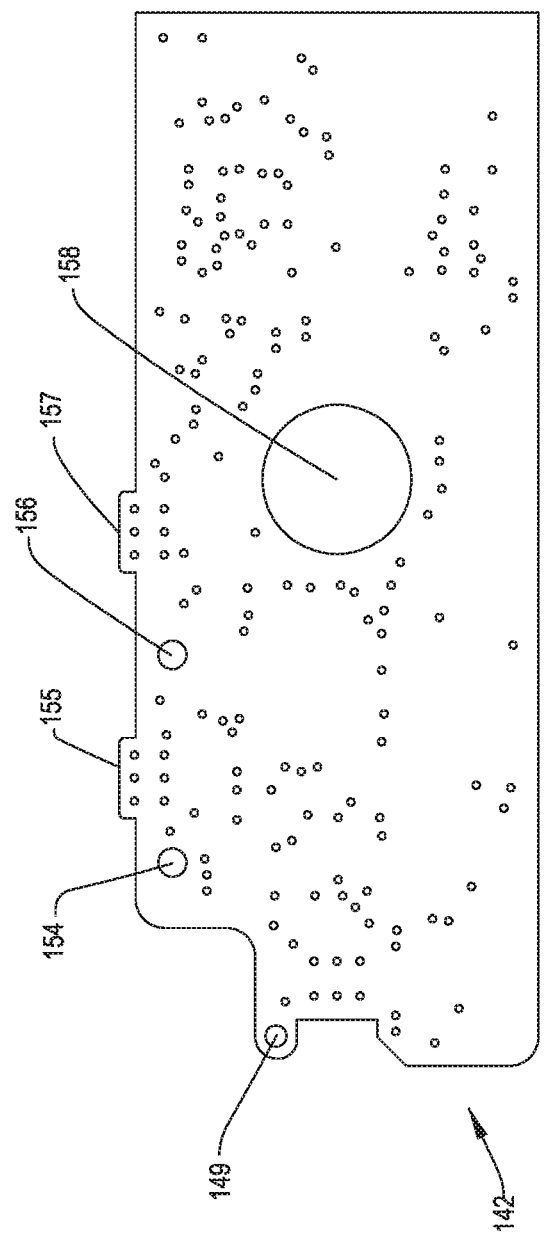
FIG. 23 is a plan view of the circuit board illustrating a plurality of bores.

A spacer 144, now described by reference to FIG. 22, is comprised of a single piece of plastic. Spacer is approximately 1.4 mm thick. Spacer 144 has a pair of through bores 146 and 148. Spacer through bores 146 and 148 are slightly larger in diameter to mount posts 182 and 186, respectively. Spacer 144 further includes a circular bore 150 and an L-shaped bore 152. Bore 150 is approximately the same diameter as an opening 158 of printed circuit board 142 (and opening 138 of printed circuit board 59), as shown in FIGS. 22, and 23. Bore 152 provides clearance for components, such as a capacitor (not identified) attached to the top surface of printed circuit board 142. The exact location of bore 152 is not defined and is a function of external components on the printed circuit board 142 requiring clearance during final assembly.

Printed circuit board 142 is now further described by reference to FIG. 23. In some versions of this invention, printed circuit board 142 of control module 40 may be replaced with previously disclosed printed circuit board 59, as shown in FIG. 5. In some versions of this invention, both printed circuit board 142 and printed circuit board 59 are present. Extending from a top edge of circuit board 142 are peninsulas 155 and 157. Each peninsula contains three equally spaced apart holes (not identified) for accepting the electrical leads of a Hall sensor 168. The three electrical leads of each sensor 168 are slip fit through the three peninsula holes. Sensors are attached to the circuit board 142 with mount 160. Sensors leads are soldered to the board. Printed circuit board 142 is further formed with an opening 158. Circuit board 142 further includes bores 149, 154 and 156. Bore 149 is located on a side edge of printed circuit board 142. Bore 149 is slightly larger in diameter than mount post 178. Bores 154 and 156 are slightly larger in diameter than mount posts 186 and 182, respectively. Each circuit board bore is slightly larger than its respective post in order to provide a clearance. This clearance is created for manufacturing reasons so that an adhesive can attach the circuit board over the mount posts. Mount 160 is secured to printed circuit board 142 using the post-in-bore arrangement seen in FIG. 19.

Shown in FIG. 24 is a lid 179. Lid 179 is an alternative embodiment of previously described lid 60 of this invention. Lid 179 is formed with all the features of lid 60.

A bottom surface of lid 179 includes a plurality of closed-end recesses 181. The shape and depth of each recess 181 is a function of the type of component located on the top surface of printed circuit board 142. Each recess 181 is dimensioned to provide clearance for an associated circuit board component, for manufacturing reasons. Recessed bores 183 and 185 are further formed on lid 179 and are close-ended. Each bore 183 is dimensioned to receive mount post 178 within the bottom surface of lid 179. Bores 185 are dimensioned to receive mount posts 182 and 186 within the bottom surface of lid 179. Cut-outs 187 are recesses within previously described rib 73 of this invention. Cut-outs 187 are cut from rib 73 to allow clearance for each associated circuit board peninsula 155 and 157. During final assembly, circuit board peninsulas 155 and 157 seat within lid cut-outs 187.

Mount 160 is fitted with sensors 162, 164 and 166 by placing mount 160 in a fixture. Once mount 160 is seated in the fixture, sensors 162 and 166 are seated within the associated mount slots 176, as shown in FIG. 19. Sensor 162 is seated within the upper slot 176 of H-shaped section 174. Digital sensors 168 are then seated within associated mounts slots 176. Sensors are inserted either by hand or by tweezers. The electrical leads of each sensor are pre-bent and cut so they slip fit into the circuit board 142. The electrical leads of motor rotor analog Hall sensors 162 and 164 are longer for manufacturing and packaging reasons.

An adhesive is next applied around the openings of the printed circuit board 142 where mount posts 178, 182, 186 are slip fit through. Analog Hall sensor 164 is seated within mount slot 176 of H-shaped section 174. Printed circuit board 142 is fitted over mount 160. In this process, the board 142 is fitted over the sensor leads so that the sensor leads seat in the corresponding openings in the board. The sensor leads are soldered to the board. Soldering bonds the outer surfaces of electrical leads to the circuit board 142. Simultaneously, mount post 178 is slip fit through circuit board bore 149, and mount posts 182 and 186 are slip fit through circuit board bores 154 and 156, respectively. Industrial adhesive is applied around the outer surface of each post to secure mount 160 to spacer 144. Owing to the clearance between each post and associated board bore, adhesive enters the space between an outer surface of each post and an inner wall of each board bore to create a stronger bond. Since three points define a plane, mount posts orient the Hall sensors to the lid 179, and then the control module 40. Mount posts assist in controlling the "X" and "Y" components with respect to the positioning of each sensor and the mount within the overall assembly. Spacer 144 controls the "Z" component with respect to the positioning of each sensor and the mount in the overall assembly.

Adhesive is then applied at select points along the top surface of the circuit board 142, and spacer 144 is fastened to the top of circuit board 142. Simultaneously, posts 182 and 186 are slip fit through spacer bores 146 and 148, respectively. Bores 146 and 148 assist in the proper orientation of the spacer with respect to the circuit board 142 and additional internal components of the control module 40.

Adhesive is then applied along the top surface of the spacer 144. Adhesive is also applied to the top face of each post 178, 182 and 186. Assembly is now secured within the bottom surface of lid 179. Spacer 144 is now attached to the control module lid 179. The top surface of spacer 144 abuts the bottom surface of lid 179. The top surface of post 178 approaches, but does not abut, the bottom surface of lid at the location of circular recess 183. The top surfaces of posts 182 and 186 approaches, but does not abut, the bottom surface of lid 179 at the location of circular recesses 185.

When the spacer 144 is seated in the bottom surface of lid 179, the circuit board, mount, and sensors, together as a sub-assembly, are now secured to the lid 179. Lid 179, with sub-assembly including: spacer, circuit board, mount and sensors, is then attached over a top opening of module shell 58. Furthermore, shell post 57 extends through opening 158 and spacer opening 150.

Consequently, analog Hall sensors 162, 164 and 166 and digital Hall sensors 168 are, by virtue of the mount 160, attached and properly oriented to the control module lid 179 and properly oriented within the control module 40. As a result, Hall sensors 162 and 164 are positioned towards the motor rotor 34. Each pair of Hall sensors 166 and 168 are positioned towards the surgical tool trigger switches 46, 47.

Another benefit of mount 160 is for ease of calibration after final tool assembly. When the powered surgical tool of this invention reaches its final point of assembly, the handpiece is calibrated for accuracy. As part of this process, the signals output by the sensors are evaluated to determine if they are within certain pre-determined performance parameters. Mount 160 secures each sensor to the circuit board 142 so that the sensors may spatially fall within the required mechanical zone for successful calibration. The mount 160 of this invention prevents each mounted Hall sensor from being displaced during, and after, all assembly stages; therefore, the surgical power tool is able to undergo calibration with greater efficacy and ease. In utilizing a mount to retain sensors in pre-determined positions within the control module, the manufacturing scrap rate is minimized due to fewer failed calibrations. Another benefit of mount 160 is that it allows for an inexpensive assembly process during manufacture. Mount 160 also provides for a spatially repeatable and reliable assembly of internal components.

In some versions of this invention, any one of mount posts 178, 182 or 186 can extend from any inner surface of the control module 40. It is not necessary that each post extend from the mount 160. In one version of this invention, at least one post extends from the mount 160.

It should also be appreciated that alternative methods of assembling the control module are within the scope of this invention. For example, in some versions of the invention the mount, with or without the sensors already fitted to the mount, is securely fitted to the control module before the sensors are attached to the circuit board.

Likewise, there is no requirement that the mount always be secured to the lid of the control module. In alternative versions of the invention, the mount may be secured to the inner surface of another panel that defines the void space of the control module.

Accordingly, it is an object of the following claims to cover all such modifications and variations that come within the true spirit and scope of this invention.

What is claimed is:

1. A control module for regulating the operation of a powered surgical tool, said control module including:
a shell, said shell configured for attachment to a powered surgical tool and said shell being formed with at least one opening;
a circuit disposed in said shell for regulating operation of a power generating unit integral with the powered surgical tool;
at least one conductive pin that extends through the at least one opening of said shell for establishing an electrical connection between the power generating unit and said circuit; and
a seal assembly disposed in said at least one opening of said shell, said seal assembly including:
a first stop disposed in the at least one opening around said pin, said first stop extending to an inner surface of said shell that defines the shell opening;
a second stop disposed in the at least one opening around said pin, said second stop extending to the inner surface of said shell that defines the shell opening and being spaced away from said first stop; and
a seal disposed in the at least one opening around said conductive pin and between said first and second stops, said seal including: a boot, said boot shaped to have: an inner skirt that extends around a section of said conductive pin that extends through the shell opening; an outer skirt that is disposed around said pin adjacent the inner surface of said shell that defines the shell opening; and a base that extends between said skirts; and at least one biasing member separate from said boot located between said skirts that biases said outer skirt against the inner surface of said shell or that biases said inner skirt against said pin.

2. The control module of claim 1, wherein:
both said boot skirts are moveable; and
said biasing member both urges said boot outer skirt against the inner surface of said shell and said boot inner skirt against said conductive pin.

3. The control module of claim 1, wherein said boot is formed from a flexible material.

4. The control module of claim 1, wherein:
said shell is formed with a plurality of openings;
a plurality of said conductive pins extend through said shell and are connected to said circuit wherein, at least two said pins extend through separate openings in said shell; and
a plurality of seal assemblies are mounted to said shell, each said seal assembly being disposed in a separate one of the shell openings around the said pin that extends through the opening.

5. The control module of claim 4, wherein at least two of said first stops of separate said seal assemblies extend from a common plate that is disposed over an outer face of said shell.

6. The control module of claim 4, wherein at least two of said second stops of separate said seal assemblies extend from a common plate that is disposed over an inner face of said shell.

7. The control module of claim 1, wherein:
said boot skirts are spaced apart from each other so as to define a gap between said skirts; and
said biasing member is a spring that is separate from said boot that is disposed in the gap between said skirts.

8. The control module of claim 1, wherein, said at least one conductive pin or said seal assembly is formed with a feature to inhibit rotation of the pin in said seal.

9. The control module of claim 8, wherein: said conductive pin is formed with an outwardly extending collar; and one of said first or second stops is formed with a tab that is positioned to be adjacent said pin collar so as to inhibit rotation of said collar and said pin.

10. The control module of claim 1, wherein said circuit is configured to control a power generating unit of a powered surgical tool that is from the group consisting of: a motor; a device that outputs electrical energy; a device that outputs thermal energy; a device that outputs photonic energy; and a device that vibrates a cutting accessory connected to the power generating unit of the surgical tool.

11. The control module of claim 1, wherein said shell includes: a base with an open face; a lid disposed over the open face of said base; and a fastener that holds said lid to said base.

12. A control module for regulating the operation of a powered surgical tool, said control module including:
a shell, said shell, shaped to be formed with at least one opening, the at least one opening being defined by an inner wall of said shell;
a circuit disposed in said shell for regulating operation of a power generating unit integral with the powered surgical tool;
at least one conductive pin that extends through the at least one opening of said shell for establishing an electrical connection between the power generating unit and said circuit;
a boot disposed in the at least one opening of said shell so as to extend around a section of said conductive pin disposed in said opening, said boot having:
an inner skirt that is disposed against said at least one pin; and
an outer skirt that is connected to and extends outwardly from said inner skirt, said outer skirt extending towards the inner wall of said shell that defines shell opening;
a spring located between said inner and outer of skirts of said boot that at least one of: biases said inner skirt against said at least one conductive pin; or biases said outer skirt against the inner wall of said shell; and
first and second stops that extend inwardly from the inner wall of said shell, said stops being spaced apart from each other and said boot and said spring being disposed between said stops, wherein said stops are mounted to said shell to prevent longitudinal movement of said boot and said spring beyond said stops.

13. The control module of claim 12, wherein:
both said skirts are moveable; and
said spring bias both said outer skirt against the inner wall of said shell and said inner skirt against said conductive pin.

14. The control module of claim 12, wherein said boot is a single piece component formed from a flexible material.

15. The control module of claim 12, wherein:
said shell is formed with a plurality of openings;
a plurality of said conductive pins extend through shell and are connected to said circuit wherein, at least two said pins extend through separate openings in said shell; and
in a plurality of the shell openings through which said conductive pins extend, an assembly consisting of a said boot, a said spring and said first and second stops are disposed in the openings around said pins.

16. The control module of claim 15, wherein at least one of:
a plurality of said first stops extend from a common plate that is disposed over an outer face of said shell; or
a plurality of said second stops extends from a common plate that is disposed over an inner face of said shell.

17. The control module of claim 12, wherein at least one of said first or second stops consists of a cap that is pressed into the at least one opening of said shell.

18. The control module of claim 12, wherein said shell is formed with a step that extends inwardly relative to the inner wall of shell that defines the at least one opening of said shell, said step being either said first said stop or said second said stop.

19. The control module of claim 12, wherein said spring is a helically wound spring that extends at least partially circumferentially around said pin.

20. The control module of claim 12, wherein:
said shell is formed with a groove that extends outwardly from the inner wall of said shell that defines the at least one opening of said shell; and
one of said first stop or said second stop is fitted to said shell so as to be seated in the groove.

21. The control module of claim 12, wherein said boot and one of said first stop or said second stop are formed as a single piece component.

22. The control module of claim 12, wherein said boot is formed as a single piece component and is further formed to have a base that extends between said inner skirt and said outer skirt.

23. The control module of claim 12, wherein said circuit is configured to control a power generating unit of a powered surgical tool that is from the group consisting of: a motor; a device that outputs electrical energy; a device that outputs thermal energy; a device that outputs photonic energy; and a device that vibrates a cutting accessory attached to the power generating unit of the surgical tool.

24. The control module of claim 12, wherein:
both said skirts are moveable; said spring is a helical spring that is positioned between said skirts to both bias said outer skirt against the inner wall of said shell and bias said inner skirt against said conductive pin; and
at least one of said first or second stops consists of a cap that is pressed into the at least one opening of said shell.

* * * * *